United States Patent [19]
Siemensmeyer et al.

[11] Patent Number: 5,833,880
[45] Date of Patent: Nov. 10, 1998

[54] POLYMERIZABLE LIQUID-CRYSTALLINE COMPOUNDS

[75] Inventors: Karl Siemensmeyer; Karl-Heinz Etzbach, both of Frankenthal; Paul Delavier; Frank Meyer, both of Ludwigshafen, all of Germany

[73] Assignee: BASF Aktiengesellschaft, Ludwigshafen, Germany

[21] Appl. No.: 682,587

[22] PCT Filed: Feb. 27, 1995

[86] PCT No.: PCT/EP95/00707

§ 371 Date: Aug. 23, 1996

§ 102(e) Date: Aug. 23, 1996

[87] PCT Pub. No.: WO95/24454

PCT Pub. Date: Sep. 14, 1995

[30] Foreign Application Priority Data

Mar. 11, 1994 [DE] Germany .......................... 44 08 171.5

[51] Int. Cl.⁶ .............................. C09K 19/20; C09K 19/52
[52] U.S. Cl. .............................. 252/299.64; 252/299.01; 252/299.67
[58] Field of Search ................... 252/299.01, 299.67, 252/299.64

[56] References Cited

U.S. PATENT DOCUMENTS

| | | | |
|---|---|---|---|
| 5,210,630 | 5/1993 | Heynderickx et al. | 359/106 |
| 5,385,690 | 1/1995 | Fimkelmann et al. | 252/299.01 |
| 5,426,009 | 6/1995 | Coates et al. | 430/20 |
| 5,538,768 | 7/1996 | Marden et al. | 428/1 |
| 5,543,075 | 8/1996 | Parri et al. | 252/299.01 |
| 5,560,864 | 10/1996 | Goulding | 252/299.01 |

FOREIGN PATENT DOCUMENTS 35 35 547   5/1986   Germany .

OTHER PUBLICATIONS

Advanced Materials, vol. 5, No. 2, pp. 107–109, 1993, Kurt Geibel, et al., "In Situ Photopolymerized, Oriented Liquid–Crystalline Diacrylates with High Thermal Conductivities".

The Journal of Chemical Physics, vol. 52, No. 2, pp. 631–637, Jan. 15, 1970, H. Baessler, et al., "Helical Twisting Power of Steroidal Solutes in Cholesteric Mesophases".

The Journal of Chemical Physics, vol. 51, No. 5, pp. 1846–1852, Sep. 1, 1969, H. Baessler, et al., "Electric Field Effects on the Dielectric Properties and Molecular Arrangements of Cholesteric Liquid Crystals".

Zeitschrift Fuer Naturforschung, vol. 28a, p. 799–800, 1973, H. Finkelmann, et al., "Helixinversion in Einem Binaeren Mischsystem Nematisch/Cholesterisch".

Die Naturwissenschaften, vol. 58, pp. 599–602, 1971, H. Stegemeyer, et al., "Induzierung Von Optischer Aktivitaet Und Zirkulardichroismus In Nematischen Phasen Durch Chirale Molekuele".

Berichte Der Bunsen–Gesellschaft Fuer Physikalische Chemie, vol. 78, No. 7, pp. 869–874, 1974, H. Finkelmann, et al., "Beschreibung Cholesterischer Mischsysteme Mit Einer Erweiterten Goossens–Theorie".

Die Makromolekulare Chemie, vol. 187, pp. 289–296, 1986, Giancarlo Galli, "Synthesis and Thermotropic Properties of New Mesogenic Diacrylate Monomers".

Festkoerper Probleme XI, Advances in Solid State Physics, pp. 99–133, 1971, H. Baessler, "Liquid Crystals".

Molecular Crystals and Liquid Crystals, vol. 203, pp. 113–126, 1991, I. Heynderickx, et al., "The Use of Cholesterically–Ordered Polymer Networks in Practical Applications".

22nd Freiburg Congress on Liquid Crystals, Paper No. 7, 1993, F.H. Kreuzer, et al., "LC–Pigments".

Die Makromolekulare Chemie, vol. 190, No. 10, pp. 3201–3215, 1985, D.J. Broer, et al., "In–Situ Photopolymerization of Oriented Liquid–Crystalline Acrylates, 4ᵃ⁾, Influence of a Lateral Methyl Substituent on Monomer and Oriented Polymer Network Properties of a Mesogenic Diacrylate".

Macromolecules, vol. 25, pp. 5759–5763, 1992, R.A.M. Hikmet, "Piezoelectric Networks Obtained by Photopolymerization of Liquid Crystal Molecules".

*Primary Examiner*—C. H. Kelly
*Attorney, Agent, or Firm*—Oblon, Spivak, McClelland, Maier & Neustadt, P.C.

[57] ABSTRACT

Mixtures of liquid-crystalline compounds comprising at least two different substances of the formula I

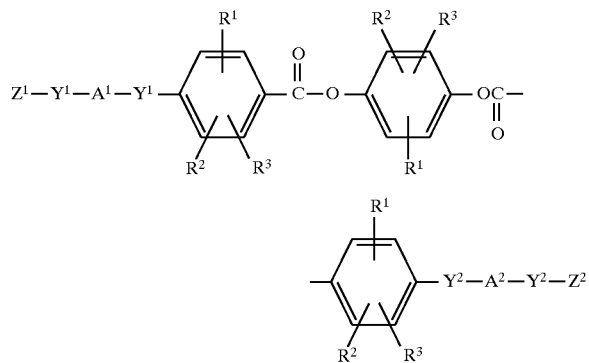

where $Z^1$ and $Z^2$, independently of one another, are polymerizable groups, $Y^1$ and $Y^2$, independently of one another, are each a direct bond, —O—, —COO—, —OCO— or —S—, $A^1$ and $A^2$, independently of one another, are spacers, and $R^1$, $R^2$ and $R^3$ are conventional substituents, and novel compounds of the above formula where at least two of $Z^1$, $Z^2$, $Y^1$, $Y^2$, $A^1$ and $A^2$ are not identical, are described. The novel mixtures and compounds are suitable, inter alia, as base material for color-effect materials and piezomaterials, preferably in chirally doped form.

16 Claims, No Drawings

POLYMERIZABLE LIQUID-CRYSTALLINE COMPOUNDS

This application is filed under 37 U.S.C. § 371 and claims benefit to PCT/EP95/00707 filed Feb. 27, 1995.

As known for molecules which are anisotropic in shape, liquid-crystalline phases, known as mesophases, can form on warming. The individual phases differ in the spatial arrangement of the major parts of the molecules on the one hand and in the molecular arrangement with respect to the long axes on the other hand (G. W. Gray, P. A. Winsor, Liquid Crystals and Plastic Crystals, Ellis Horwood Limited, Chichester, 1974). The nematic liquid-crystalline phase is distinguished by the fact that there is only one alignment long-distance order due to the long molecular axes lining up in parallel. Under the prerequisite of the molecules making up the nematic phase being chiral, a cholesteric phase forms, in which the long axes of the molecules form a helical superstructure perpendicular thereto (H. Baessler, Festköperprobleme XI, 1971). The chiral moiety may either be present in the liquid-crystalline molecule itself or be added to the nematic phase as a dope, with induction of the cholesteric phase. This phenomenon was first studied in cholesterol derivatives (eg. H. Baessler, M. M. Labes, J. Chem. Phys., 52 (1970) 631; H. Baessler, T. M. Laronge, M. M. Labes, J. Chem. Phys., 51 (1969) 799; H. Finkelmann, H. Stegemeyer, Z. Naturforschg. 28a (1973) 799; H. Stegemeyer, K. J. Mainusch, Naturwiss., 58 (1971) 599, H. Finkelmann, H. Stegemeyer, Ber. Bunsenges. Phys. Chem. 78 (1974) 869).

The cholesteric phase has remarkable optical properties: a large optical rotation value and pronounced circular dichroism caused by selective reflection of circular-polarized light within the cholesteric layer. The different colors observed depending on the viewing angle depend on the pitch of the helical superstructure, which is itself dependent on the twisting power of the chiral component. The pitch and thus the wavelengths range of the selectively reflected light of a cholesteric layer can be varied, in particular by changing the concentration of a chiral dope. Cholesteric systems of this type offer interesting opportunities for practical use. For example, incorporation of chiral moieties into mesogenic acrylic esters and alignment in the cholesteric phase, for example after photocrosslinking, allows the production of a stable, colored network, but the concentration of the chiral component therein can then no longer be changed (G. Galli, M. Laus, A. Angelon, Makromol. Chemie, 187 (1986) 289). Furthermore, admixing of non-crosslinkable, chiral compounds wit:h nematic acrylic esters and photocrosslinking allows the production of a colored polymer still containing high proportions of soluble components (I. Heyndricks, D. J. Broer, Mol. Cryst. Liq. Cryst. 203 (1991) 113). Furthermore, the random hydrosilylation of mixtures of cholesterol derivatives and acrylate-containing mesogens using defined cyclic siloxanes followed by photopolymerization allows the production of a cholesteric network in which the chiral component can have a proportion of up to 50% of the material employed; however, these polymers still contain significant amounts of soluble components (F. H. Kreuzer, R. Maurer, C. M üller-Rees, J. Stohrer, Paper No. 7, 22nd Freiburg congress on liquid crystals, Freiburg, 1993).

DE-A-35 35 547 describes a process in which a mixture of cholesterol-containing monoacrylates can be converted into cholesteric layers by photocrosslinking. However, the total proportion of the chiral component in the mixture is about 94%. Although, as a pure side-chain polymer, a material of this type is not very mechanically stable, an increase in the stability can, however, be achieved by means of highly crosslinking diluents.

EP-A 331 233 describes mixtures of liquid-crystalline compounds which are symmetrically substituted by aliphatic side chains.

In addition to the nematic and cholesteric networks described above, smectic networks are also known and can be prepared, in particular, by photopolymerization/photocrosslinking of smectic liquid-crystalline materials in the smectic liquid-crystalline phase. The materials used for this purpose are generally symmetrical, liquid-crystalline bisacrylates, as described, for example, by D. J. Broer and R. A. M. Hikmet, Makromol. Chem., 190 (1989) 3201–3215. However, these materials have very high clearing points of >120° C., with the attendant risk of thermal polymerization. If an $S_c$ phase is present, piezoelectric properties can be achieved by admixing chiral materials (R. A. M. Hikmet, Macromolecules 25 (1992) 5759).

It is an object of the present invention to prepare novel polymerizable nematic liquid-crystalline materials which, alone or in mixtures with other polymerizable nematic liquid crystals, have broad nematic phase ranges and clearing points of below 120° C. and which can be processed at below 120° C.

We have found that this object is achieved by liquid-crystalline mixtures comprising at least two different compounds of the formula I

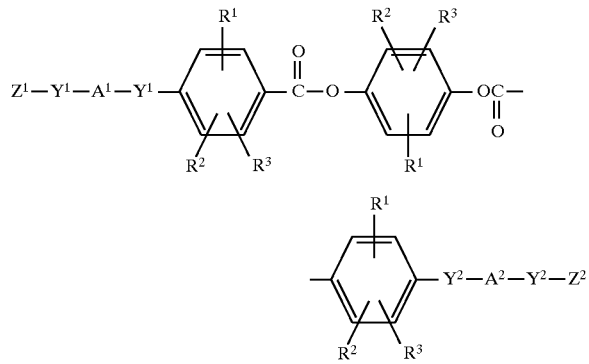

where $Z^1$ and $Z^2$, independently of one another, are polymerizable groups, $Y^1$ and $Y^2$, independently of one another, are each a direct bond, —O—, —COO—,—OCO— or —S—, $A^1$ and $A^2$, independently of one another, are spacers, and $R^1$, $R^2$ and $R^3$, independently of one another, are hydrogen, $C_1$- to $C_{20}$-alkyl$^1$, $C_1$- to $C_{20}$-alkoxy, $C_1$- to $C_{20}$-alkoxycarbonyl, $C_1$- $_{to}$ $C_{20}$-monoalkylaminocarbonyl, formyl, $C_1$- to $C_{20}$-alkylcarbonyl, fluorine, chlorine, bromine, cyano, $C_1$- to $C_{20}$-alkylcarbonyloxy, $C_1$- to $C_{20}$-alkylcarbonylamino, hydroxyl or nitro, with the proviso that $-A^1-Y^1$- and $-A^2-Y^2$- in at least one of the substances I are different O-alkylene radicals.

$Z^1$ and $Z^2$ are preferably groups which can be polymerized by a photochemical initiation step, ie., in particular, groups of the structure $CH_2$=CH—, $CH_2$=CCl—, $CH_2$=C($CH_3$)— or 4-vinylphenyl. Preference is given to $CH_2$=CH—, $CH_2$=CCl— and $CH_2$=C($CH_3$)—, and particular preference is given to $CH_2$=CH— and $CH_2$=C($CH_3$)—.

Besides a direct bond, $Y^1$ and $Y^2$ are, in particular, ether and ester groups. The spacers $A^1$ and $A^2$ can be all groups known for this purpose. The spacers are usually linked to Z via ester or ether groups or via a direct bond. The spacers generally contain from 0 to 30, preferably from 2 to 12, carbon atoms and may be interrupted in the chain, for example by O, S, NH or $NCH_3$. Suitable substituents for the spacer chain are fluorine, chlorine, bromine, cyano, methyl and ethyl. Examples of representative spacers are $(CH_2)_p$, $(CH_2CH_2O)_qCH_2CH_2$, $(CH_2CH_2S)_qCH_2CH_2$, $(CH_2CH_2NH)_qCH_2CH_2$,

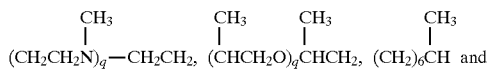

where q is from 1 to 3, and p is from 1 to 12.

$R^1$, $R^2$ and $R^3$ in the mixture components of the formula I can be hydrogen or substituents of the type indicated in claim 1. Preference is given to radicals which suppress the formation of smectic phases and promote the formation of nematic phases. One of the radicals R is preferably hydrogen, and in particular two radicals R are hydrogen. Of said radicals, preference is given to chlorine, bromine, cyano, fluorine, hydroxyl, methyl, ethyl, methoxy, ethoxy, methoxycarbonyl, formyl, acetyl and acetoxy, and also longer-chain radicals having ≧8 carbon atoms.

The moieties

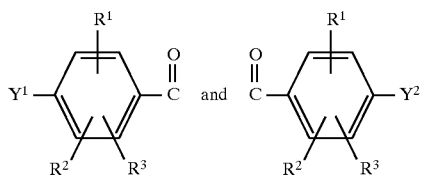

in the compounds of the formula I in the mixtures in claim 1 preferably have, independently of one another, one of the following structures:

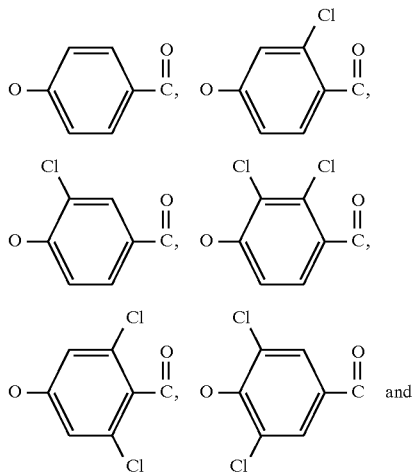

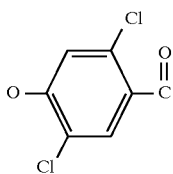

or analogous structures with Cl replaced by F, Br, $CH_3$, $OCH_3$, CHO, $COCH_3$, $OCOCH_3$ or CN, where the substituents can also be mixed. Mention should furthermore be made of the structures

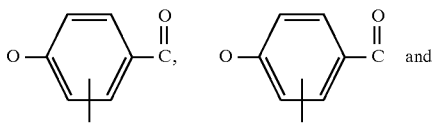

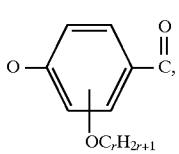

where r is from 2 to 20, preferably from 8 to 15.

The moiety

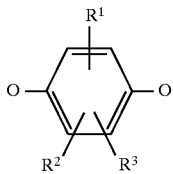

in formula I preferably conforms to the formulae:

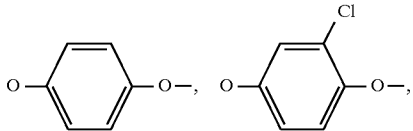

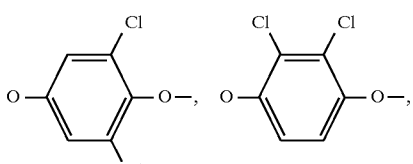

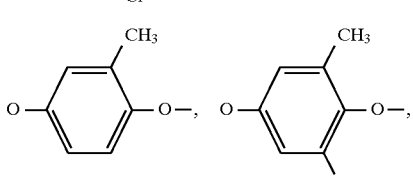

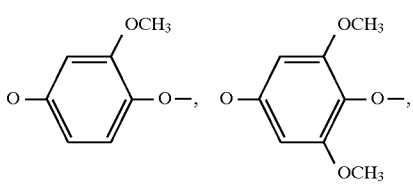

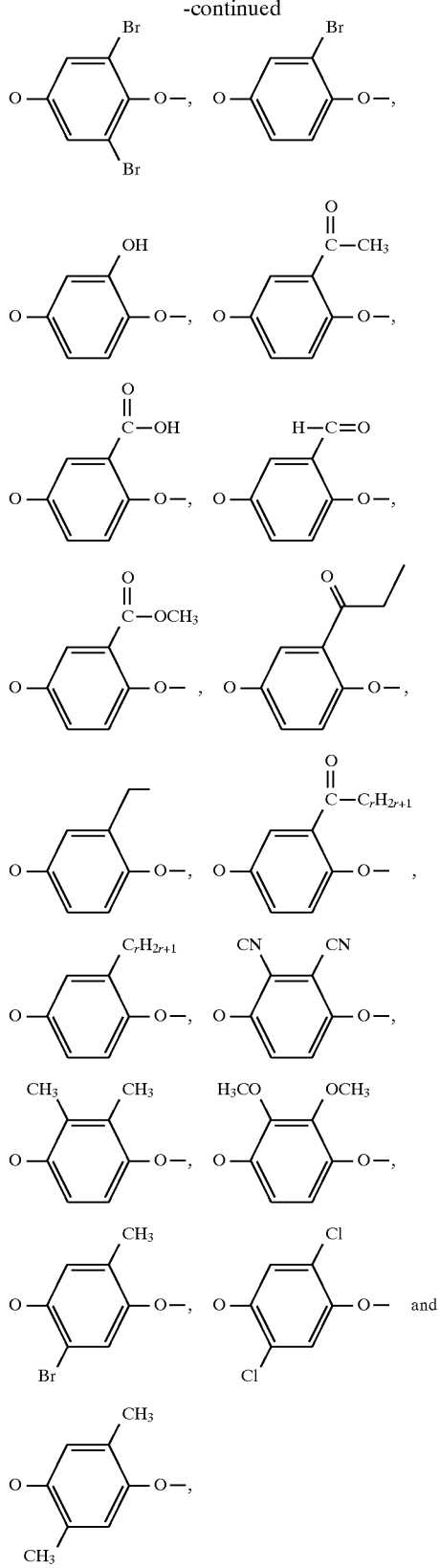

where r is a number from 2 to 20, preferably from 8 to 15.

Particularly suitable components for the novel mixtures are the novel compounds as claimed in claim 9. The surprisingly different crystallization behavior of the individual components means that the liquid-crystalline state range of the mixtures as claimed in claim 1 is significantly broadened.

The mixtures and the compounds of the formula I can be prepared by methods known per se. Details on the preparation are given in the examples. The compounds of the formula I are liquid-crystalline and can form smectic or nematic phases, depending on the structure. The novel compounds and mixtures are suitable for all purposes for which liquid-crystalline compounds are usually used.

The novel mixtures and compounds, alone, in mixtures with one another or with other liquid-crystalline compounds, have phase structures like low-molecular-weight liquid crystals, but can be converted into highly crosslinked polymers with a frozen liquid-crystalline ordered structure by free-radical or ionic polymerization processes.

In order to establish desired properties of the mixtures, it may be expedient to use more than two compounds of the formula I or alternatively combinations of novel mixtures with other polymerizable liquid crystals, it also being possible to prepare such mixtures by mechanical mixing. The tailoring of the phase state ranges is also possible, in particular, by adding non-liquid-crystalline polymerizable components, known as reactive thinners, for example hexanediol diacrylate or bisphenol A diacrylate. The addition of reactive thinners has a favorable effect, in particular, on the flow viscosity. The novel mixtures are particularly suitable as alignment layers for liquid-crystalline materials, as photocrosslinkable adhesives, as monomers for the preparation of liquid-crystalline networks, as base material for the production of polymerizable liquid-crystal systems which can be doped by chiral compounds, as polymerizable matrix monomers for polymer-dispersed displays, as base material for polymerizable liquid-crystalline materials for optical components, for example polarizers, retardation plates, lenses and, with chiral dopes, as base material for color-effect materials and piezomaterials.

The invention furthermore relates to novel compounds of the formula I where $R^1$ to $R^3$, $Z^1$, $Z^2$, $Y^1$, $Y^2$, $A^1$ and $A^2$ are as defined above, and —$A^1$—$Y^1$— and —$Y^2$—$A^2$— are not simultaneously identical —O-alkylene radicals.

EXAMPLES

The following abbreviations are used throughout the examples:
c crystalline phase
n nematic phase
ch cholesteric phase
s smectic phase (not characterized in greater detail)
i isotropic phase.

The phase transition temperatures were determined using a polarizing microscope. Temperatures were measured in a Mettler FP 80/82 microscope heating stage.

The monomers used as mixture components all contain polymerizable groups. In the case of these materials, the polymerization can be initiated photochemically, by means of conventional free-radical formers or alternatively thermally. It should therefore be ensured during preparation of the mixtures that polymerization does not commence.

General procedure for the preparation of the nematic or chiral nematic (cholesteric) mixtures:

The mixture components are dissolved in methylene chloride, giving an isotropic solution. The methylene chloride is then removed under reduced pressure at approximately 40° to 60° C.

EXAMPLE 1

Preparation of 1-[4'-(4''-acryloxybutoxy) benzoyloxy]-4-[4'-(2''-acryloxyethyloxy) benzoyloxy]benzene 4-(4'-Hydroxybutoxy)benzoic acid (1):

4-Chlorobutyl acetate (276.6 g; 1.8 mol) is added to a solution of ethyl 4-hydroxybenzoate (249 g; 1.5 mol), potassium iodide (3 g) and potassium carbonate (248 g; 1.8 mol) in dimethylformamide (2 l), and the mixture is stirred at 90° C. for 11 hours. The reaction mixture is transferred into 5 l of ice water, and the resultant precipitate is filtered off with suction and washed with 4 to 5 l of ice water. The crude product is dissolved in 3 l of ethanol, potassium hydroxide (400 g) is added, and the mixture is refluxed for 3 hours. The reaction mixture is transferred into 6 l of ice water, and acidified by means of concentrated hydrochloric acid, and the precipitate is filtered off, washed with water until neutral and then dried.

Yield: 282.1 g (89%).

4-(4'-Acryloxybutoxy)benzoic acid (2):

A solution of (1) (282 g; 1.34 mol), freshly distilled acrylic acid (230 ml; 3.35 mol), hydroquinone (1.9 g) and p-toluenesulfonic acid (23.7 g) in 1,1,1-trichloroethane (1.1 l) is refluxed for 10 hours. The reaction mixture is cooled to from 60° to 70° C. and stirred into 2.5 l of petroleum ether, and the precipitate is filtered off, washed with petroleum ether and dried at room temperature under reduced pressure for 24 hours.

Yield: 299.3 g (84%).

4-[4'-(4-Acryloxybutoxy)benzoyloxy]phenol (3):

Oxalyl chloride (10 ml) is added at 0° C. to (2) (5 g; 19 mmol), and the mixture is stirred until the evolution of gas subsides (20 min). The excess oxalyl chloride is removed by distillation in a water-pump vacuum, the acid chloride is taken up in toluene (10 ml), the toluene solution is added at 0° C. to a solution of hydroquinone (10.5 g; 95 mmol) in pyridine (10 ml) and toluene (5 ml), and the mixture is subsequently stirred at room temperature for 24 hours. The reaction mixture is then transferred into water (200 ml), and the mixture is extracted twice with dichloromethane (50 ml each time). The organic extracts are dried using calcium chloride, hydroquinone (50 mg) is added to the filtrate, and the mixture is evaporated in a water-pump vacuum. The residue is chromatographed on silica gel (toluene/ethyl acetate (5:1), giving 4.5 g (66%) of (3).

1-[4'-(4''-Acryloxybutoxy)benzoyloxy]-4-[4'-(2''-acryloxyethoxy)-benzoyloxy]benzene (4):

Oxalyl chloride (10 ml) is added at 0° C. to 4-(2'-acryloxyethoxy)-benzoic acid (4.3 g; 16.3 mmol), and the mixture is stirred until the evolution of gas subsides (30 min). The excess oxalyl chloride is removed by distillation in a water-pump vacuum, the acid chloride is taken up in toluene (10 ml), the toluene solution is added at 0° C. to a solution of (3) (5.8 g; 16.3 mmol) in pyridine (10 ml) and toluene (5 ml), and the mixture is subsequently stirred at room temperature for 13 hours. The reaction mixture is then transferred into water (200 ml), and the mixture is extracted twice with dichloromethane (50 ml each time). The organic extracts are dried using calcium chloride, hydroquinone (50 mg) is added to the filtrate, and the mixture is evaporated in a water-pump vacuum. The residue is chromatographed on silica gel (toluene/ethyl acetate (5:1), giving 7.8 g (83%) of (4).

The following compounds are prepared by a method similar to that in Example 1:

| Ex. | $Z^1-Y^1-$ | $A^1$ | $T^1$ | $T^2$ | $T^3$ | $A^2$ | $Y^2-Z^2$ |
|---|---|---|---|---|---|---|---|
| 2 | acryloyl | $C_4H_8$ | 4-oxybenzoyloxy | 2-Cl-phenylene | 4-oxybenzoyl | $C_2H_4$ | acryloyl |
| 3 | " | " | " | " | " | $C_6H_{12}$ | " |
| 4 | " | $C_6H_{12}$ | " | " | " | $C_{11}H_{22}$ | " |
| 5 | " | $C_2H_4$ | " | " | " | $C_8H_{16}$ | " |
| 6 | " | $C_4H_8$ | " | 2-CH$_3$-phenylene | " | $C_2H_4$ | " |
| 7 | " | $C_2H_{12}$ | " | " | " | $C_8H_{16}$ | " |

-continued $$Z^1-Y^1-A^1-\left[\underset{T^1}{\underbrace{Y^1-\underset{R^2\ R^3}{\overset{R^1}{\bigcirc}}-\overset{\phantom{O}}{\underset{\phantom{O}}{C}}-O}}\underset{T^2}{\underbrace{\overset{R^2\ R^3}{\underset{R^1}{\bigcirc}}}}\underset{T^3}{\underbrace{O\overset{\phantom{O}}{\underset{O}{C}}-\underset{R^2\ R^3}{\overset{R^1}{\bigcirc}}-Y^2}}\right]-A^2-Y^2-Z^2$$

| Ex. | $Z^1-Y^1-$ | $A^1$ | $T^1$ | $T^2$ | $T^3$ | $A^2$ | $Y^2-Z^2$ |
|---|---|---|---|---|---|---|---|
| 8 | " | $C_4H_8$ | " | 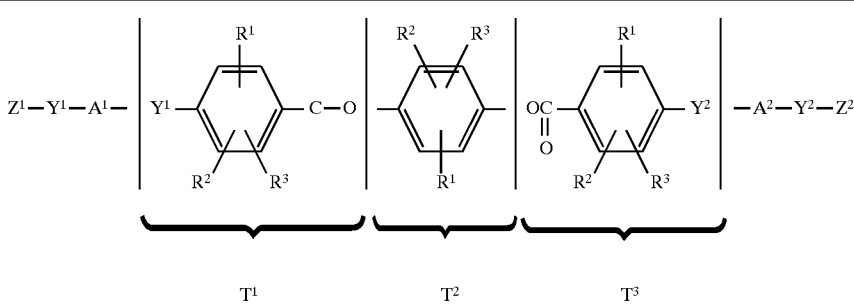 | " | $C_6H_{12}$ | " |
| 9 | " | $C_2H_4$ | " | " | " | $C_8H_{16}$ | " |
| 10 | " | " | " | 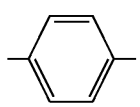 | " | " | " |
| 11 | " | $C_4H_8$ | " | 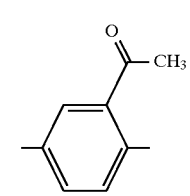 | " | " | " |
| 12 | " | " | " | 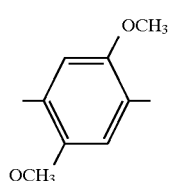 | " | " | " |
| 13 | " | " | " | 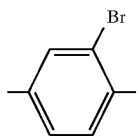 | " | " | " |
| 14 | " | " | " | 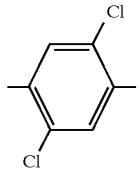 | " | " | " |
| 15 | " | " | " | 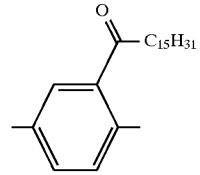 | " | " | " |

-continued $$Z^1-Y^1-A^1-\left[\underbrace{Y^1-\underset{R^2}{\overset{R^1}{\bigcirc}}-\underset{R^3}{C-O}}_{T^1}\ \underbrace{\underset{R^1}{\overset{R^2}{\bigcirc}}}_{T^2}\ \underbrace{\underset{R^2}{\overset{R^1}{OC}}-\underset{R^3}{\bigcirc}-Y^2}_{T^3}\right]-A^2-Y^2-Z^2$$

| Ex. | $Z^1-Y^1-$ | $A^1$ | $T^1$ | $T^2$ | $T^3$ | $A^2$ | $Y^2-Z^2$ |
|---|---|---|---|---|---|---|---|
| 16 | " | " | " | 2-Cl phenylene | " | $C_2H_4$ | " |
| 17 | " | " | " | " | " | $C_6H_{12}$ | " |
| 18 | " | $C_2H_4$ | " | " | " | " | " |
| 19 | " | $C_6H_{12}$ | " | " | " | $C_2H_4$ | " |
| 20 | " | $C_2H_4$ | " | " | " | $C_6H_{12}$ | " |
| 21 | " | " | " | " | " | $C_{11}H_{22}$ | " |
| 22 | " | $C_4H_8$ | " | " | " | $C_8H_{16}$ | " |
| 23 | " | " | " | " | " | $C_{11}H_{22}$ | " |
| 24 | " | " | " | 2-CH$_3$ phenylene | " | $C_2H_4$ | " |
| 25 | " | $C_6H_{12}$ | " | " | " | $C_8H_{16}$ | " |
| 26 | " | " | " | " | " | $C_2H_4$ | " |
| 27 | " | $C_2H_4$ | " | " | " | $C_6H_{12}$ | " |
| 28 | " | $C_6H_{12}$ | " | " | " | $C_{11}H_{22}$ | " |
| 29 | " | $C_{11}H_{22}$ | " | " | " | $C_6H_{12}$ | " |
| 30 | " | $C_2H_4$ | " | " | " | " | " |
| 31 | " | $C_6H_{12}$ | " | " | " | $C_2H_4$ | " |
| 32 | " | $C_2H_4$ | " | " | " | $C_8H_{16}$ | " |
| 33 | " | $C_8H_{16}$ | " | " | " | $C_2H_4$ | " |
| 34 | " | $C_2H_4$ | " | " | " | $C_{11}H_{22}$ | " |
| 35 | " | $C_{11}H_{22}$ | " | " | " | $C_2H_4$ | " |
| 36 | " | $C_4H_8$ | " | " | " | $C_6H_{12}$ | " |
| 37 | " | $C_6H_{12}$ | " | " | " | $C_4H_8$ | " |
| 38 | " | $C_4H_8$ | " | " | " | $C_8H_{16}$ | " |
| 39 | " | $C_8H_{16}$ | " | " | " | $C_4H_8$ | " |
| 40 | " | $C_4H_8$ | " | " | " | $C_{11}H_{22}$ | " |
| 41 | " | $C_{11}H_{22}$ | " | " | " | $C_4H_8$ | " |
| 42 | CH$_2$=C(CH$_3$)C(O)O- | $C_4H_8$ | " | phenylene | " | " | " |
| 43 | CH$_2$=CHC(O)O- | $C_6H_{12}$ | " | 2-Cl phenylene | " | " | -O-CH=CH$_2$ |
| 44 | " | $C_4H_8$ | " | 2-C$_8$H$_{17}$ phenylene | " | $C_6H_{12}$ | -O-C(O)CH=CH$_2$ |

-continued
| Ex. | $Z^1-Y^1-$ | $A^1$ | $T^1$ | $T^2$ | $T^3$ | $A^2$ | $Y^2-Z^2$ |
|---|---|---|---|---|---|---|---|
| 45 | " | " | 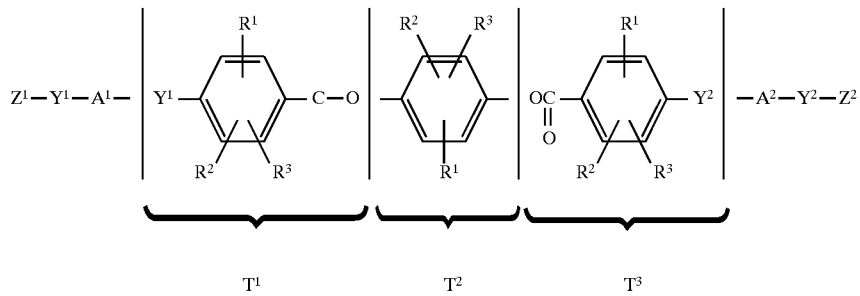 | 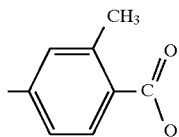 | 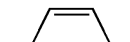 | " | " |
| 46 | " | " | 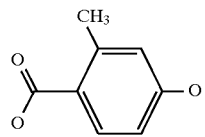 | 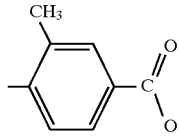 | 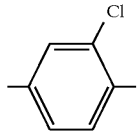 | " | " |
| 47 | " | $C_6H_{12}$ | 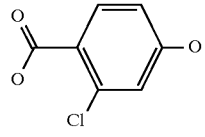 | 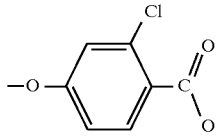 | 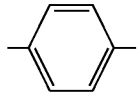 | $C_4H_8$ | 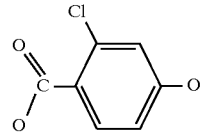 |
| 48 | " | " | " | " | 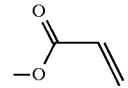 | " | " |
| 49 | 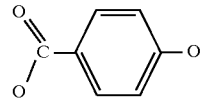 | " | 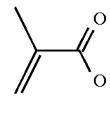 | " | " | " | " |
| 50 | 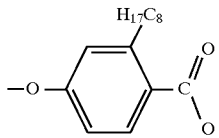 | " | 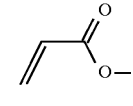 | " | 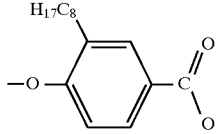 | " | " |
| 51 | " | $C_8H_{16}$ | " | 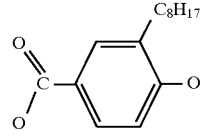 | " | $C_2H_4$ | " |

EXAMPLE 52

Mixture 1:

| Component | Structure | Concentration (mol %) |
|---|---|---|
| K1 | CH$_2$=CH-CO-O-C$_6$H$_{12}$-O-C$_6$H$_4$-CO-O-C$_6$H$_4$-O-CO-C$_6$H$_4$-O-C$_6$H$_{12}$-O-CO-CH=CH$_2$ | 50 |
| K2 | CH$_2$=CH-CO-O-C$_6$H$_{12}$-O-C$_6$H$_4$-CO-O-C$_6$H$_3$(Cl)-O-CO-C$_6$H$_4$-O-C$_6$H$_{12}$-O-CO-CH=CH$_2$ | 50 |

Phase behavior: c 50 n 98 i

EXAMPLE 53

Mixture 2:

| Component | Structure | Concentration (mol %) |
|---|---|---|
| K1 | CH$_2$=CH-CO-O-C$_6$H$_{12}$-O-C$_6$H$_4$-CO-O-C$_6$H$_4$-O-CO-C$_6$H$_4$-O-C$_6$H$_{12}$-O-CO-CH=CH$_2$ | 50 |
| K2 | CH$_2$=CH-CO-O-C$_6$H$_{12}$-O-C$_6$H$_4$-CO-O-C$_6$H$_3$(CH$_3$)-O-CO-C$_6$H$_4$-O-C$_6$H$_{12}$-O-CO-CH=CH$_2$ | 50 |

Phase behavior: c 82 n 104 i

EXAMPLE 54

Mixture 3:

| Component | Structure | Concentration (mol %) |
|---|---|---|
| K1 | CH$_2$=CH-CO-O-C$_6$H$_{12}$-O-C$_6$H$_4$-CO-O-C$_6$H$_4$-O-CO-C$_6$H$_4$-O-C$_6$H$_{12}$-O-CO-CH=CH$_2$ | 50 |

| Component | Structure | Concentration (mol %) |
|---|---|---|
| K2 | (acrylate–O–C₄H₈–O–C₆H₄–C(O)O–C₆H₄–OC(O)–C₆H₄–O–C₄H₈–O–acrylate) | 50 |

Phase behavior: c 98 n 106 i

EXAMPLE 55

Mixture 4:

| Component | Structure | Concentration (mol %) |
|---|---|---|
| K1 | (acrylate–O–C₆H₁₂–O–C₆H₄–C(O)O–C₆H₄–OC(O)–C₆H₄–O–C₆H₁₂–O–acrylate) | 48.125 |
| K2 | (acrylate–O–C₄H₈–O–C₆H₄–C(O)O–C₆H₄–OC(O)–C₆H₄–O–C₄H₈–O–acrylate) | 48.125 |
| K3 | (acrylate–O–C₂H₄–O–biphenyl–C(O)O–dianhydrosorbitol–OC(O)–biphenyl–O–C₂H₄–O–acrylate) | 3.75 |

Phase behavior: s 96 n 104 i

Color: red

EXAMPLE 56

Mixture 5:

| Component | Structure | Concentration (mol %) |
|---|---|---|
| K1 | (acrylate–O–C₄H₈–O–C₆H₄–C(O)O–C₆H₃(Cl)–OC(O)–C₆H₄–O–C₆H₁₂–O–acrylate) | 24 |

| Component | Structure | Concentration (mol %) |
|---|---|---|
| K2 | acrylate–O–C₆H₁₂–O–[benzene]–C(=O)O–[Cl-benzene]–OC(=O)–[benzene]–O–C₆H₁₂–O–acrylate | 24 |
| K3 | acrylate–O–C₄H₈–O–[benzene]–C(=O)O–[Cl-benzene]–OC(=O)–[benzene]–O–C₄H₈–O–acrylate | 24 |
| K4 | acrylate–O–C₆H₁₂–O–[benzene]–C(=O)O–[Cl-benzene]–OC(=O)–[benzene]–O–C₄H₈–O–acrylate | 24 |
| K5 as K3, mixture 4 | | 4 |

Phase behavior: s 57 ch 76 i
Color: blue-green

EXAMPLE 57

Mixture 6:

| Component | Structure | Concentration (mol %) |
|---|---|---|
| K1 | as K1–K4, mixture 5 | 25 |
| K2 | | 25 |
| K3 | | 25 |

-continued

| Component | Structure | Concentration (mol %) |
|---|---|---|
| K4 | | 25 |

Phase behavior: s 60 n 97 i

EXAMPLE 58

Mixture 7:

| Component | Structure | Concentration (mol %) |
|---|---|---|
| K1 | as K1–K4, mixture 5 | 21.71 |
| K2 | | 21.71 |
| K3 | | 21.71 |
| K4 | | 21.71 |
| K5 | 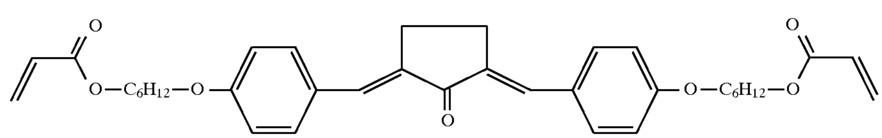 | 9.65 |

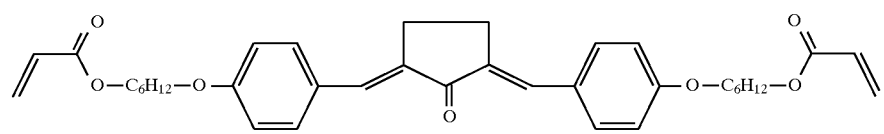

| K6 as K3, mixture 4 | | 3.5 |

Phase behavior: s 60 ch 97 i
Color: red-green

EXAMPLE 59
Mixture 8:
| Component | Structure | Concentration (mol %) |
|---|---|---|
| K1 | | 21.71 |
| K2 | | 21.71 |
| K3 | as mixture 7 | 21.71 |
| K4 | | 21.71 |
| K5 | 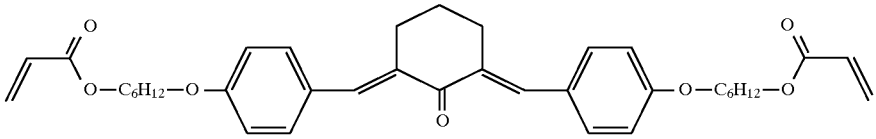 | 9.65 |
| K6 as mixture 7 | | 3.5 |
Phase behavior: s 55 ch 95 i
Color: green
EXAMPLE 60
Mixture 9:
| Component | Structure | Concentration (mol %) |
|---|---|---|
| K1 | | 21.71 |
| K2 | | 21.71 |
| K3 | as K₁–K₄ as mixture 7 | 21.71 |
| K4 | | 21.71 |
| K5 | 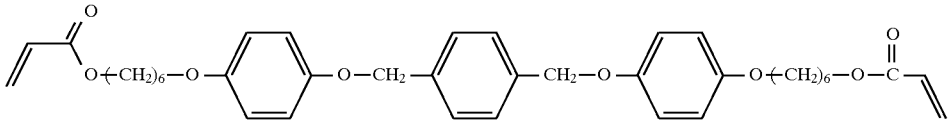 | 9.65 |
| K6 as K6, mixture 7 | | 3.5 |
Phase behavior: s 55 ch 94 i
Color: red/green
EXAMPLE 61
Mixture 10:
| Component | Structure | Concentration (mol %) |
|---|---|---|
| K1 | 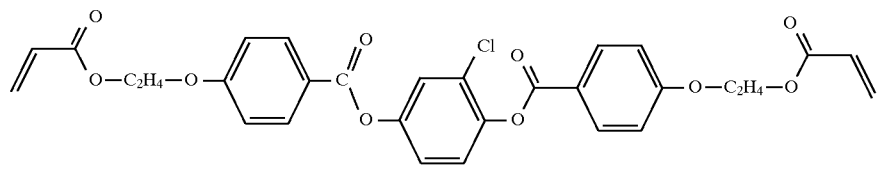 | 11.12 |
| K2 | 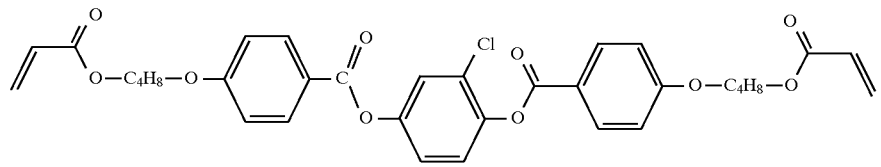 | 11.11 |

-continued

| Component | Structure | Concentration (mol %) |
|---|---|---|
| K3 | acrylate-O-C₆H₁₂-O-C₆H₄-C(=O)-O-[2-Cl-C₆H₃]-O-C(=O)-C₆H₄-O-C₆H₁₂-O-acrylate | 11.11 |
| K4 | acrylate-O-C₂H₄-O-C₆H₄-C(=O)-O-[2-Cl-C₆H₃]-O-C(=O)-C₆H₄-O-C₄H₈-O-acrylate | 11.11 |
| K5 | acrylate-O-C₂H₄-O-C₆H₄-C(=O)-O-[2-Cl-C₆H₃]-O-C(=O)-C₆H₄-O-C₆H₁₂-O-acrylate | 11.11 |
| K6 | acrylate-O-C₄H₈-O-C₆H₄-C(=O)-O-[2-Cl-C₆H₃]-O-C(=O)-C₆H₄-O-C₂H₄-O-acrylate | 11.11 |
| K7 | acrylate-O-C₄H₈-O-C₆H₄-C(=O)-O-[2-Cl-C₆H₃]-O-C(=O)-C₆H₄-O-C₆H₁₂-O-acrylate | 11.11 |
| K8 | acrylate-O-C₆H₁₂-O-C₆H₄-C(=O)-O-[2-Cl-C₆H₃]-O-C(=O)-C₆H₄-O-C₂H₄-O-acrylate | 11.11 |
| K9 | acrylate-O-C₆H₁₂-O-C₆H₄-C(=O)-O-[2-Cl-C₆H₃]-O-C(=O)-C₆H₄-O-C₄H₈-O-acrylate | 11.11 |

Phase behavior: s 11 n 101 i

EXAMPLE 62

Mixture 11:

Components of mixture 10, each in a concentration of 10.8%.

K6 from mixture 7 in a concentration of 1.99%.

Phase behavior: s 34 ch 92 i

Colorless

EXAMPLE 63

Mixture 12:

Components of mixture 10, each in a concentration of 10.78%

K6 from mixture 7 in a concentration of 2.98%.

Phase behavior: s 44 ch 90 i

Color: red

EXAMPLE 64

Mixture 13:

Components of mixture 10, each in a concentration of 10.72 mol %.

K6 from mixture 7 in a concentration of 3.52 mol %.

Phase behavior: s 51 n 80 i

Color: green

EXAMPLE 65

Mixture 14:

Components of mixture 10, each in a concentration of 10.67 mol %.

K6 from mixture 7 in a concentration of 3.97 mol %.
Phase behavior: s 65 ch 75 i
Color: blue-green

EXAMPLE 66

Mixture 15:
Components of mixture 10, each in a concentration of 9.61 mol %.

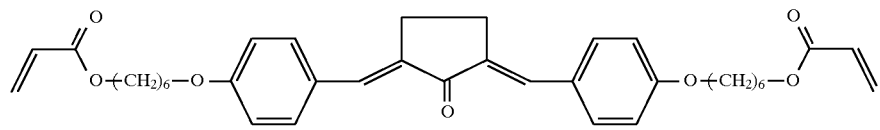

in a concentration of 10 mol %.
K6 from mixture 7 in a concentration of 3.51 mol %.
Phase behavior: s 63 ch 96 i
Color: green

EXAMPLE 67

Mixture 16:
Components of mixture 10, each in a concentration of 8.5 mol %.

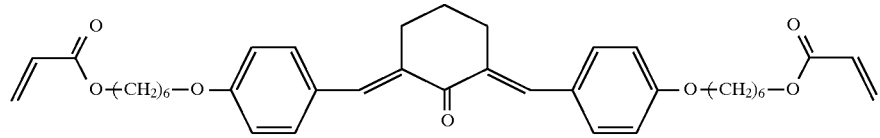

in a concentration of 10 mol %.
K6 from mixture 7 in a concentration of 3.5 mol %.
Phase behavior: s 51 n 87 i
Color: green

EXAMPLE 68

Mixture 17:
Components of mixture 10, each in a concentration of 9.61 mol %.

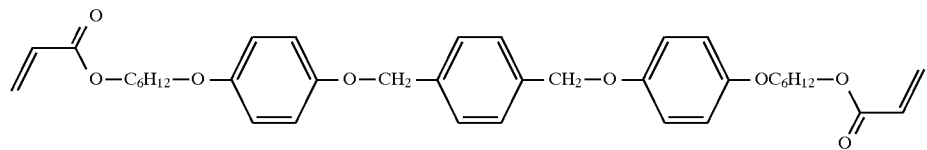

in a concentration of 10 mol %.
K6 from mixture 7 in a concentration of 3.51 mol %.
Phase behavior: s 63 ch 78 i
Color: green

EXAMPLE 69

Mixture 18:

Components K1 to K9 from mixture 10, each in a concentration of 10.67 mol %.

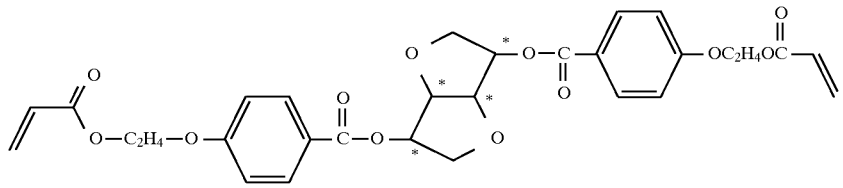

in a concentration of 3.97 mol %.
Phase behavior: ch 91 i
Colorless

EXAMPLE 70

Mixture 19:

Components of mixture 10, each in a concentration of 9.61 mol %.
Hexanediol diacrylate in a concentration of 10 mol %.
K6 from mixture 7 in a concentration of 3.51 mol %.
Phase behavior: s 50 ch 70 i
Color: green

EXAMPLE 72

Mixture 20:

Components of mixture 10, each in a concentration of 8.5 mol %.
Hexanediol diacrylate in a concentration of 20 mol %.
K6 from mixture 7 in a concentration of 3.5 mol %.
Phase behavior: s 46 ch 61 i
Color: green

EXAMPLE 73

Mixture 21:

Components of mixture 10, each in a concentration of 8.5 mol %.

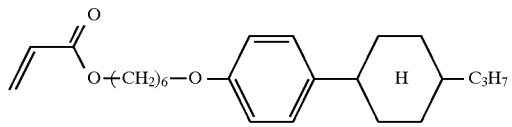

in a concentration of 20 mol %.
K6 from mixture 7 in a concentration of 3.5 mol %.
Phase behavior: s 56 ch 80 i
Color: green to red

EXAMPLE 74

Mixture 22:

Components of mixture 10, each in a concentration of 8.5 mol %.

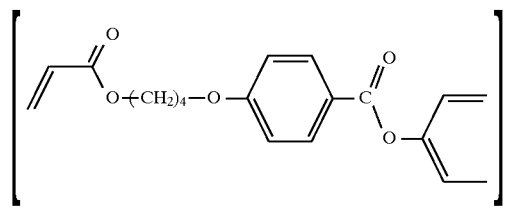

in a concentration of 20 mol %.
K6 from mixture 7 in a concentration of 3.5 mol %.

Phase behavior: s 50 ch 82 i
Color: green

EXAMPLE 75

Mixture 23:

Components of mixture 10, each in a concentration of 8.5 mol %.

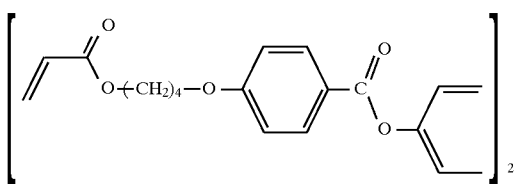

in a concentration of 20 mol %.
K6 from mixture 7 in a concentration of 3.5 mol %.
Phase behavior: s 49 ch 80.5 i

EXAMPLE 76

Mixture 24:

Components of mixture 10, each in a concentration of 8.5 mol %.

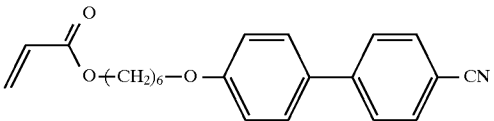

in a concentration of 20 mol %.
K6 from mixture 7 in a concentration of 3.5 mol %.
Phase behavior: s 53 ch 84 i
Color: green

EXAMPLE 77

Mixture 25:

Components of mixture 10, each in a concentration of 10.1 mol %.
K10 from mixture 18 in a concentration of 9.1 mol %.
Phase behavior: ch 89 i
Color: blue

EXAMPLE 78

Mixture 26:

Components K1 to K9 from mixture 10, each in a concentration of 10.55%.

K10 5.05

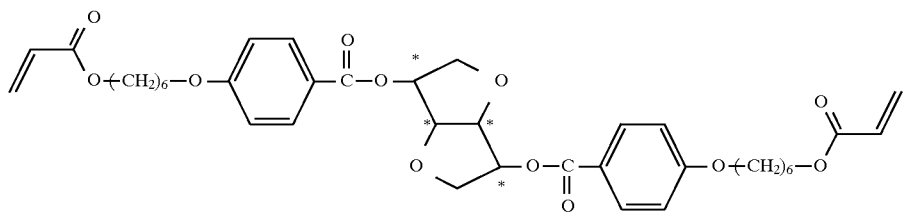

Phase behavior: ch 91 i
Color: red

EXAMPLE 79
Mixture 27:
Components K1 to K9 from mixture 10, each in a concentration of 10.33%.
Component K10 from mixture 26 in a concentration of 7.03%.
Phase behavior: ch 90 i
Color: blue

EXAMPLE 80
Mixture 28:
Components K1 to K9 from mixture 10, each in a concentration of 6.51 mol %.
Styrene in a concentration of 41.41 mol %.
Phase behavior: ch 61–74 i

EXAMPLE 81
Mixture 29:
Components K1 to K9 from mixture 10, each in a concentration of 5.22 mol %.
Styrene in a concentration of 53.02 mol %.
Phase behavior: ch 50–69 i

EXAMPLE 82
Mixture 30:

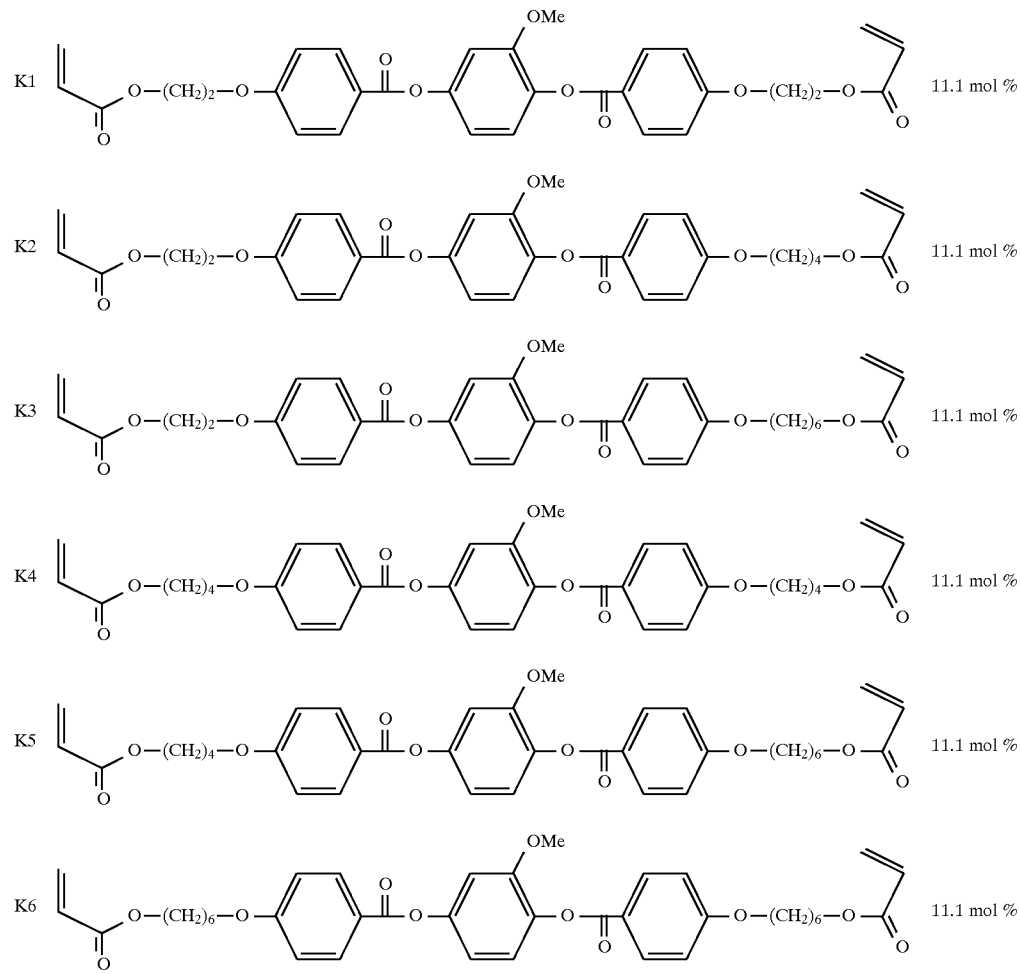

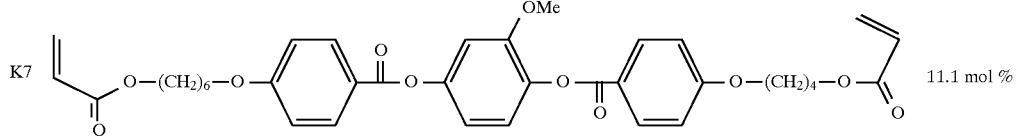 K7 ... 11.1 mol %
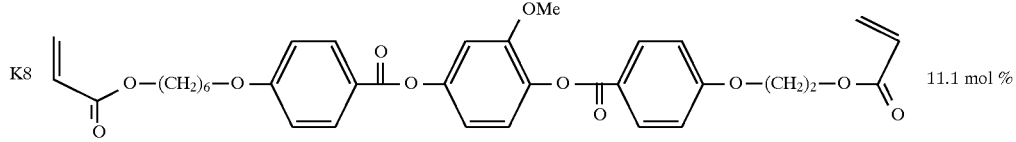 K8 ... 11.1 mol %
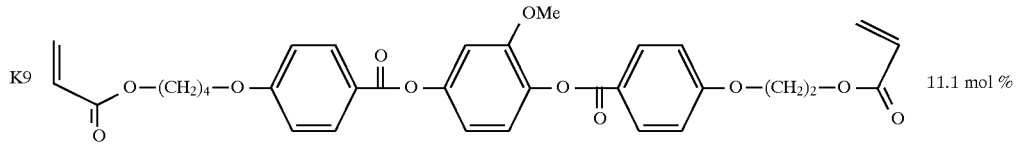 K9 ... 11.1 mol %
Phase behavior: C<25N 43–48 I
EXAMPLE 83
Mixture 31:
K1 to K9 as K1 to K9 in mixture 30, each in a concentration of 10.6 mol %
K10 as K10 in mixture 26 in a concentration of 4.6 mol %
Phase behavior: C<25N* 45–49 I
EXAMPLE 84
Mixture 32:
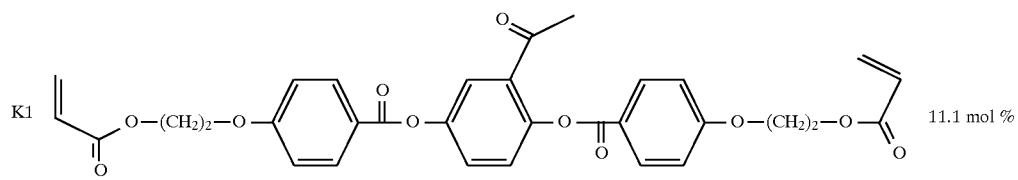 K1 ... 11.1 mol %
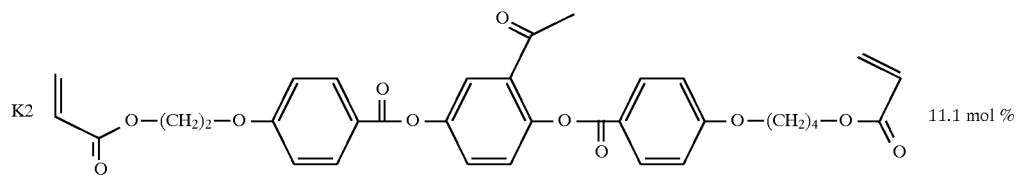 K2 ... 11.1 mol %
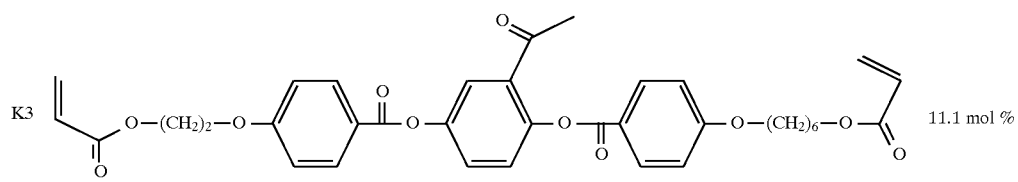 K3 ... 11.1 mol %
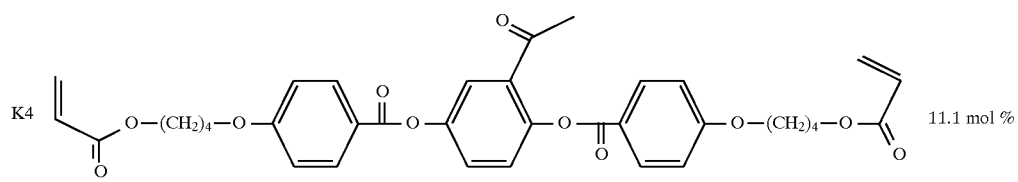 K4 ... 11.1 mol %
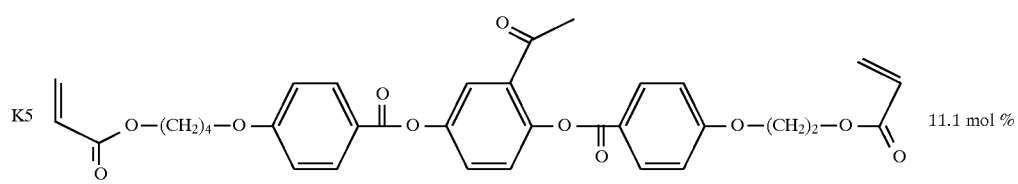 K5 ... 11.1 mol %

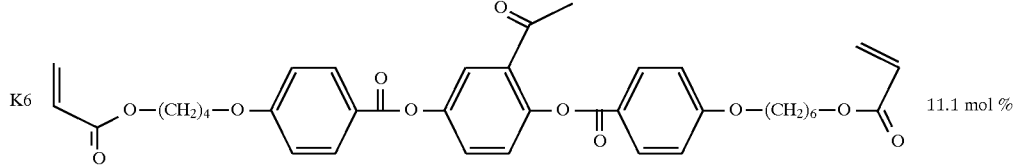 K6  11.1 mol %
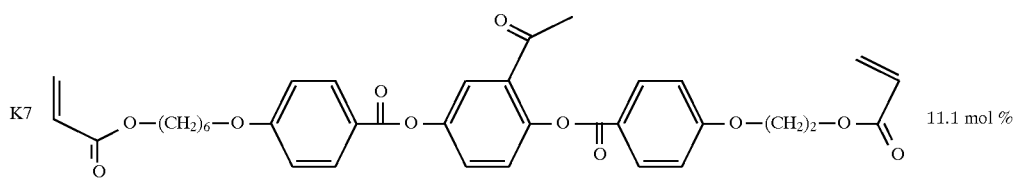 K7  11.1 mol %
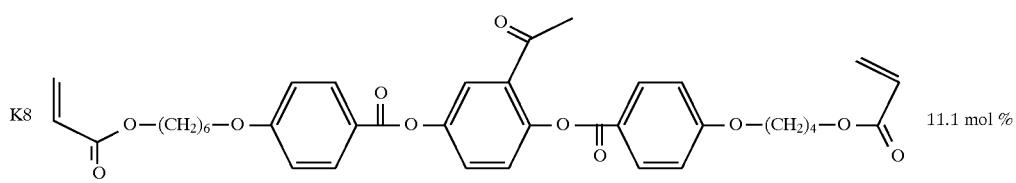 K8  11.1 mol %
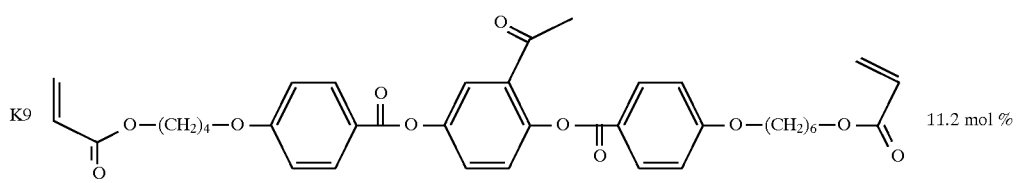 K9  11.2 mol %
Phase behavior: C<25N 36–39 I
EXAMPLE 85
Mixture 33:
K1 to K9 as K1 to K9 in mixture32, each in a concentration of 10.6 mol %
K10 as K10 in mixture 26 in a concentration of 4.6 mol %
Phase behavior: C<25N* 46–47 I
EXAMPLE 86
Mixture 34:
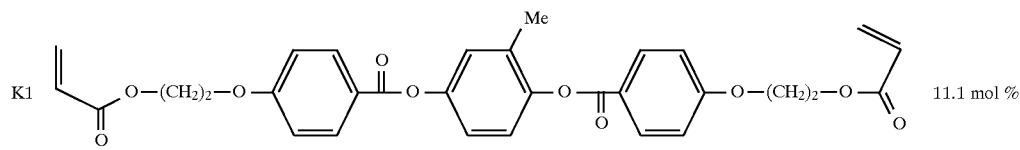 K1  11.1 mol %
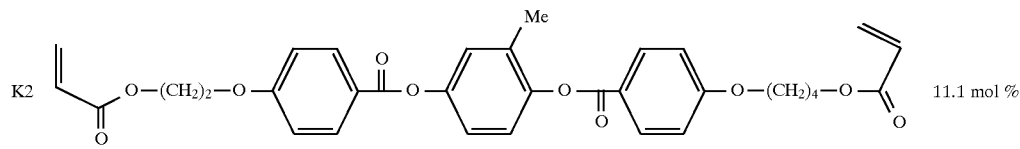 K2  11.1 mol %
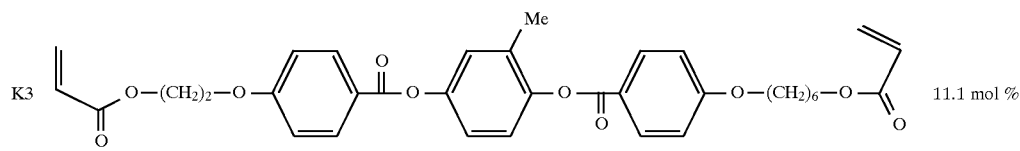 K3  11.1 mol %
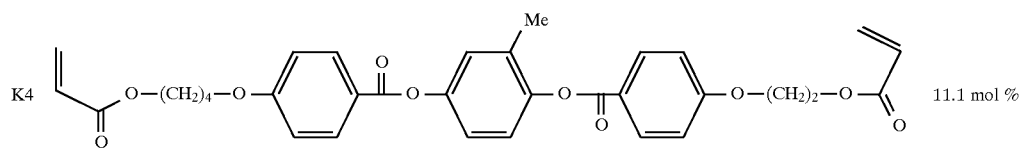 K4  11.1 mol %

-continued
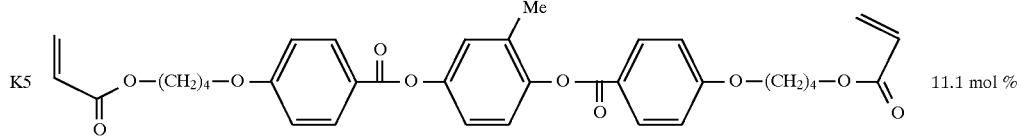 11.1 mol %
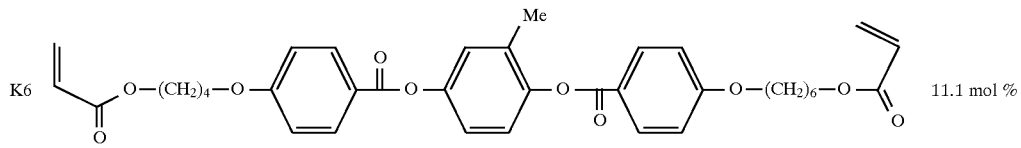 11.1 mol %
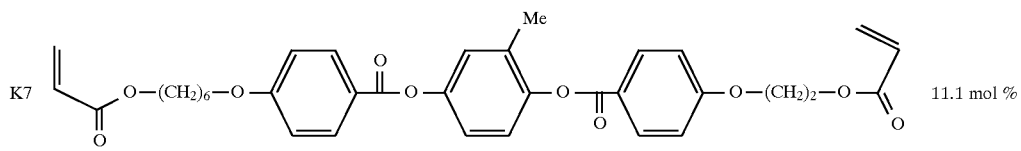 11.1 mol %
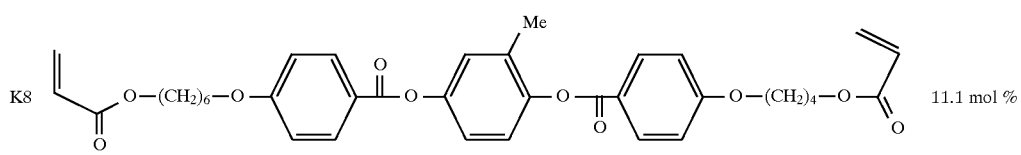 11.1 mol %
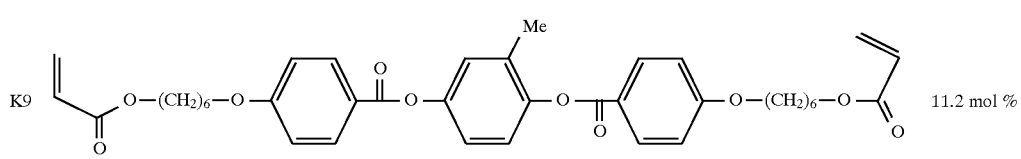 11.2 mol %
Phase behavior: C<25N 78–81 I
EXAMPLE 87
Mixture 35:
K1 to K9 as K1 to K9 in mixture 34, each in a concentration of 10.6 mol %
K10 as K10 in mixture 26 in a concentration of 4.6 mol %
Phase behavior: C<25N* 78–81 I
EXAMPLE 88
Mixture 36:
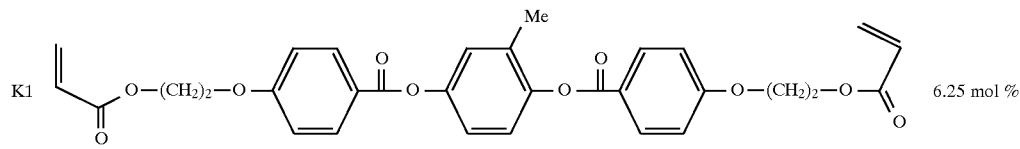 6.25 mol %
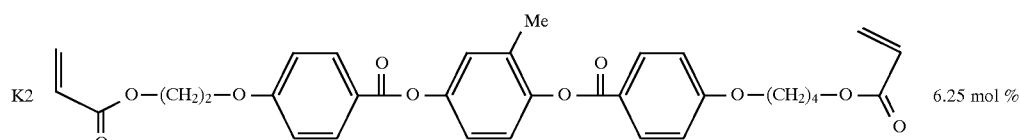 6.25 mol %
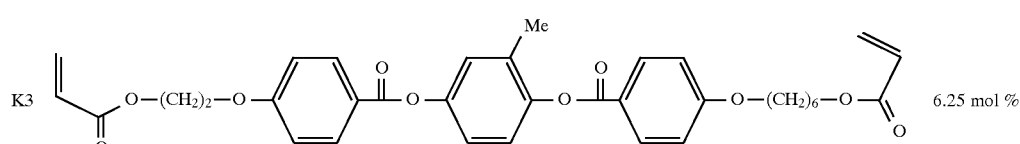 6.25 mol %
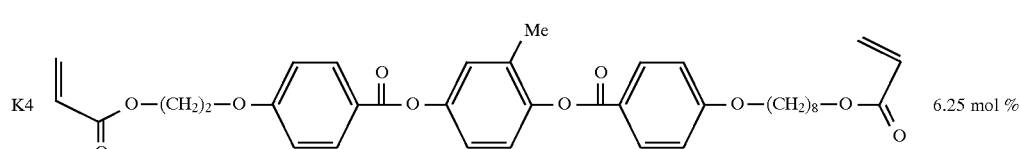 6.25 mol %

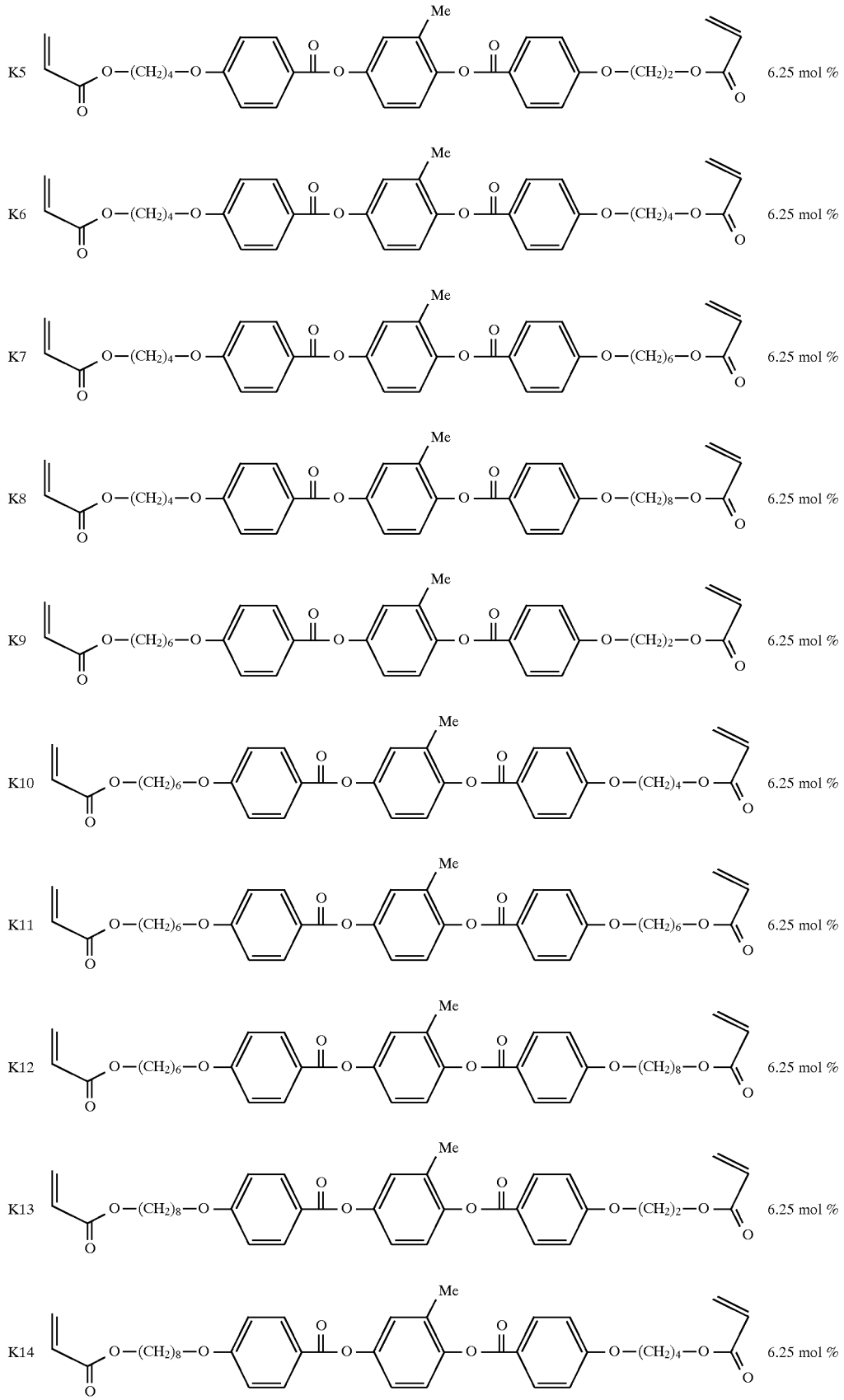

-continued
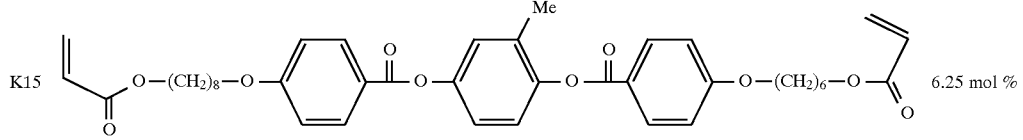
K15    6.25 mol %
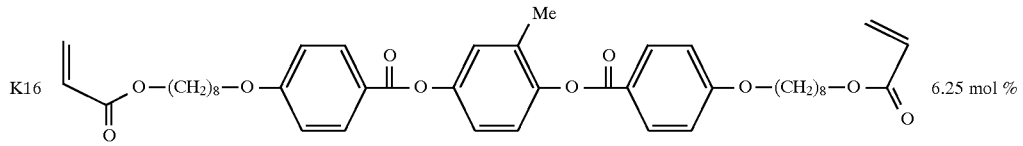
K16    6.25 mol %
Phase behavior: C<25N 66–67 I
EXAMPLE 89
Mixture 37:
K1 to K16 as K1 to K16 in mixture 36, each in a concentration of 5.6 mol %
K17 as K10 in mixture 26 in a concentration of 5.6 mol %
Phase behavior: C<25N* 63–66 I
EXAMPLE 90
Mixture 38:
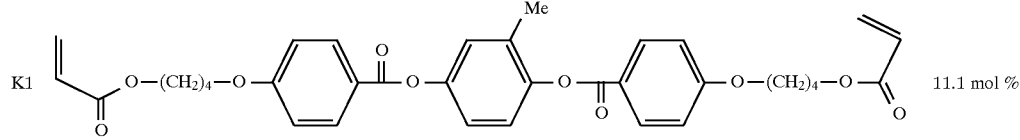
K1    11.1 mol %
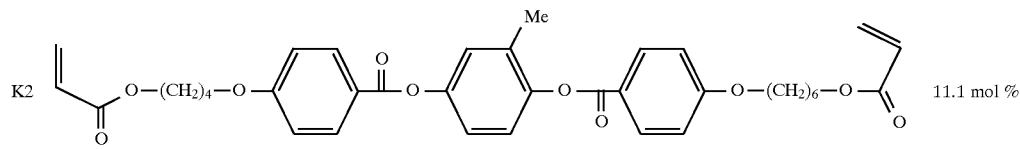
K2    11.1 mol %
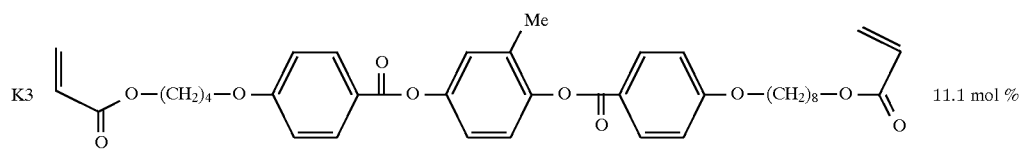
K3    11.1 mol %
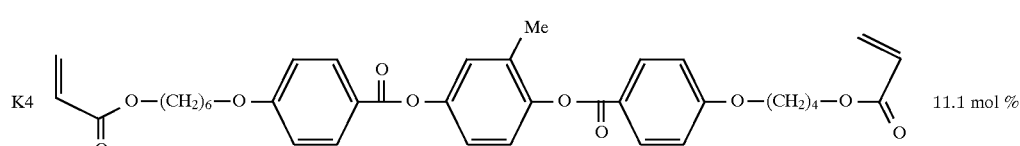
K4    11.1 mol %
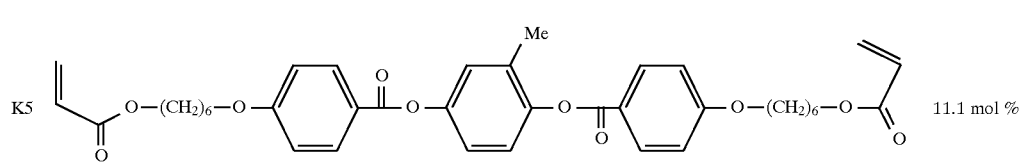
K5    11.1 mol %
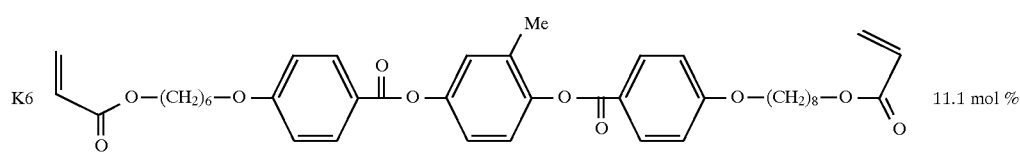
K6    11.1 mol %
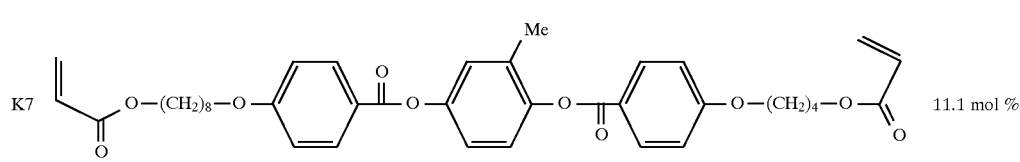
K7    11.1 mol %

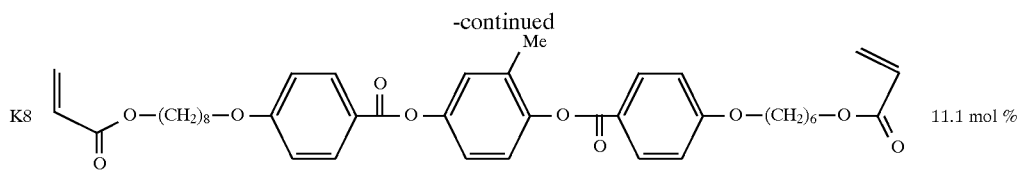 11.1 mol %
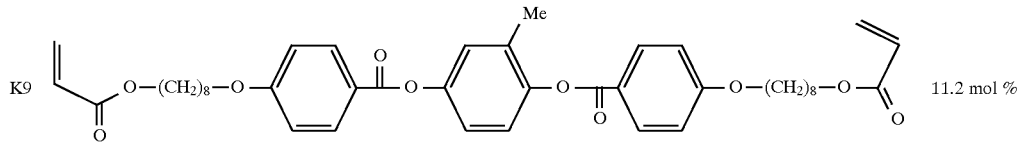 11.2 mol %
Phase behavior: C<25N 81–83 I
EXAMPLE 91
Mixture 39:
K1 to K9 as K1 to K9 in mixture 38, each in a concentration of 10.6 mol %
K10 as K10 in mixture 26 in a concentration of 4.6 mol %
Phase behavior: C<25N* 80–82 I
EXAMPLE 92
Mixture 40:
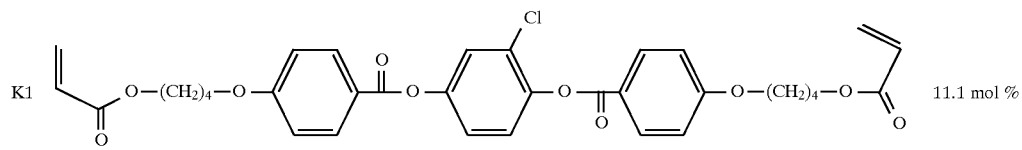 11.1 mol %
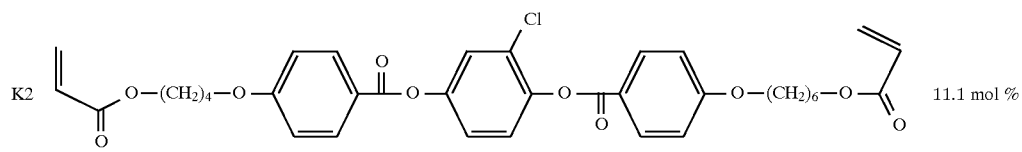 11.1 mol %
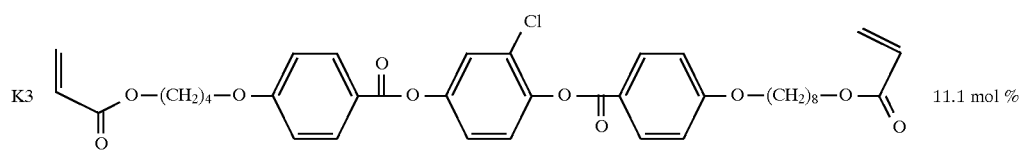 11.1 mol %
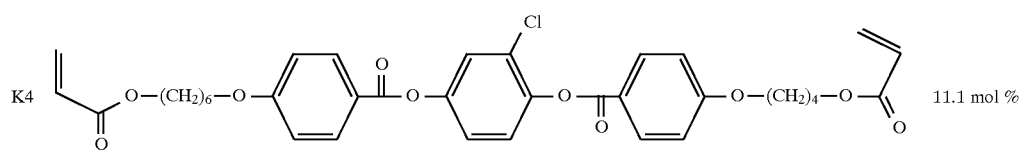 11.1 mol %
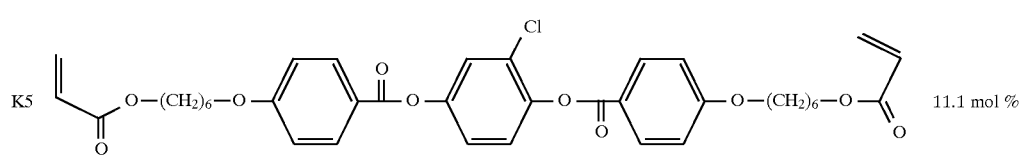 11.1 mol %
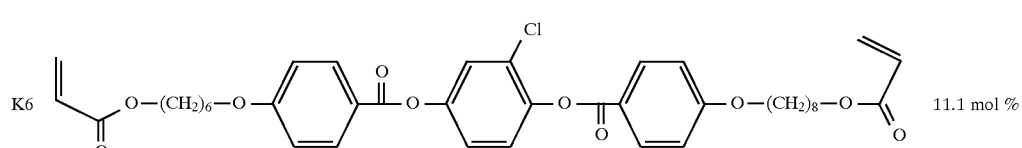 11.1 mol %
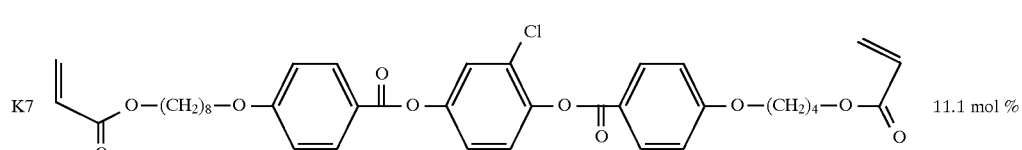 11.1 mol %

-continued
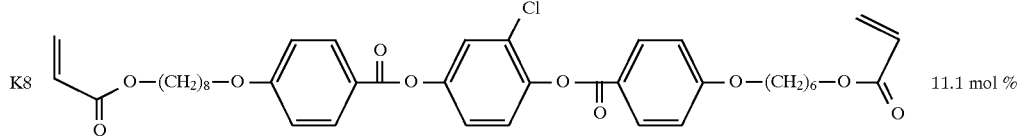 11.1 mol %
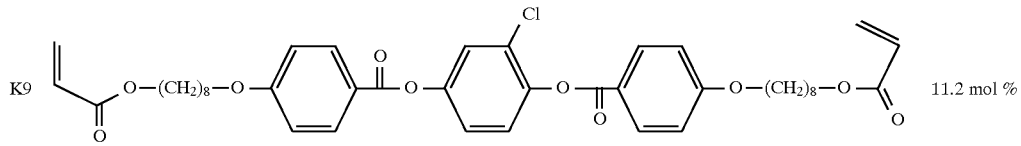 11.2 mol %
Phase behavior: C 32N 93–95 I
EXAMPLE 93
Mixture 41:
K1 to K9 as K1 to K9 in mixture 40, each in a concentration of 10.6 mol %
K10 as K10 in mixture 26 in a concentration of 4.6 mol %
Phase behavior: C 25N* 87–90 I
EXAMPLE 94
Mixture 42:
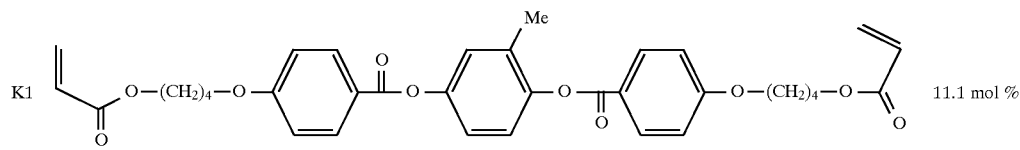 11.1 mol %
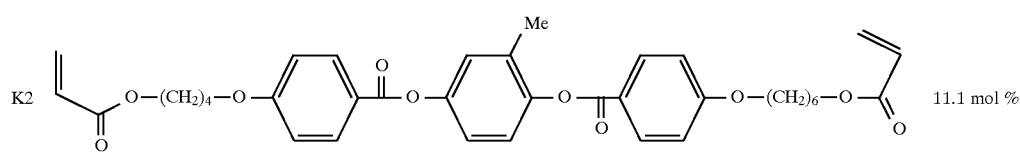 11.1 mol %
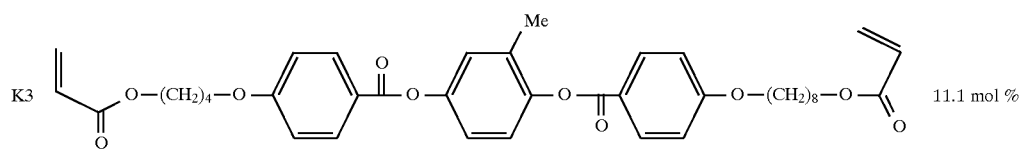 11.1 mol %
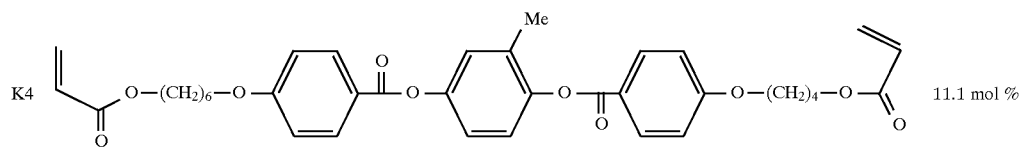 11.1 mol %
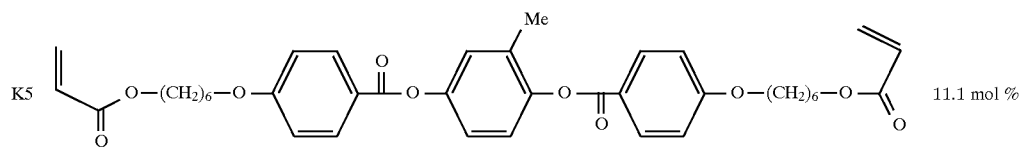 11.1 mol %
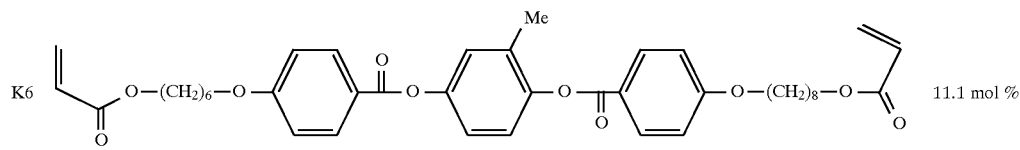 11.1 mol %
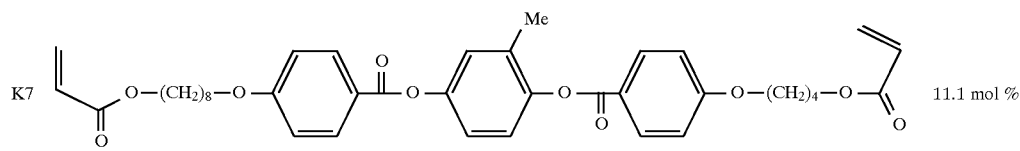 11.1 mol %

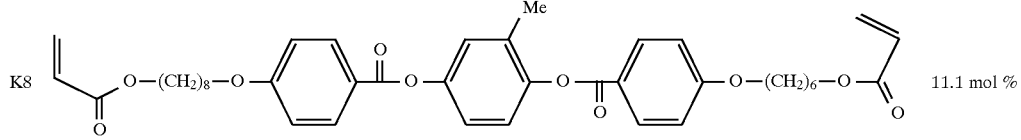 11.1 mol %
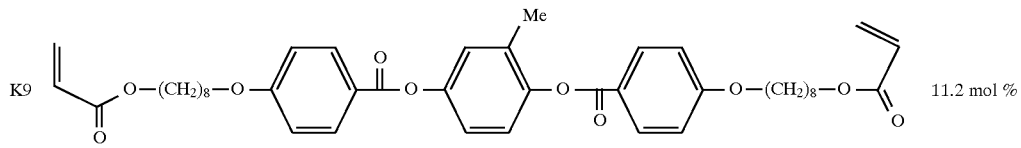 11.2 mol %
Phase behavior: C<25N 81–83 I
EXAMPLE 95
Mixture 43:
K1 to K9 as K1 to K9 in mixture 42, each in a concentration of 10.6 mol %
K10 as K10 in mixture 26 in a concentration of 4.6 mol %
Phase behavior: C<25N* 81–82 I
EXAMPLE 96
Mixture 44:
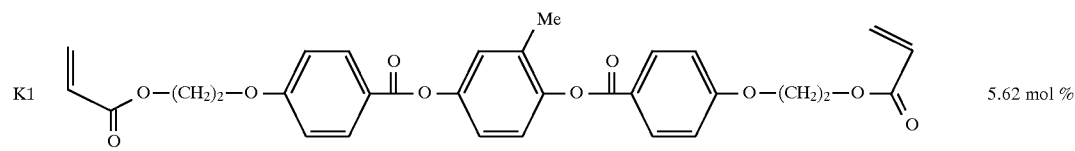 5.62 mol %
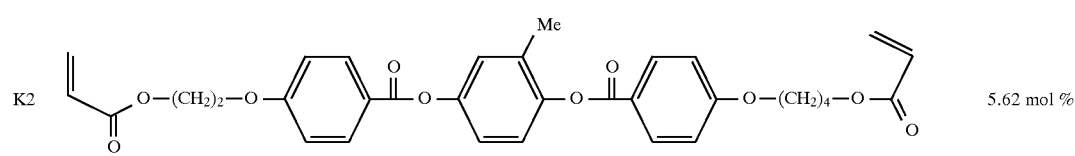 5.62 mol %
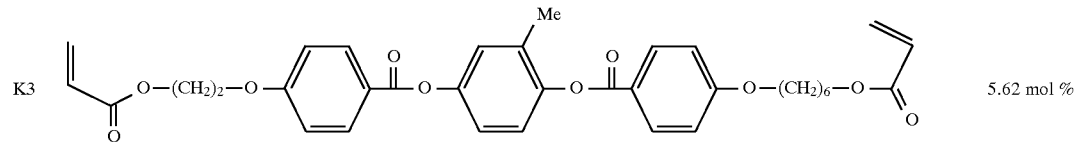 5.62 mol %
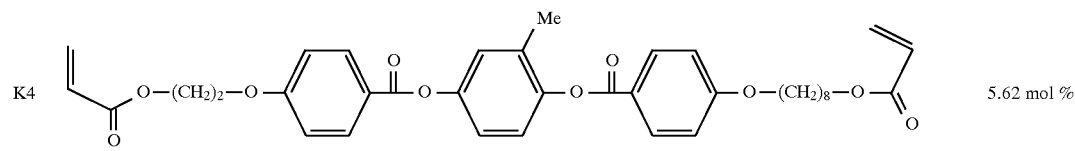 5.62 mol %
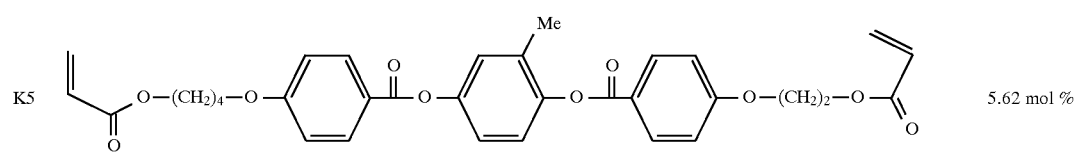 5.62 mol %
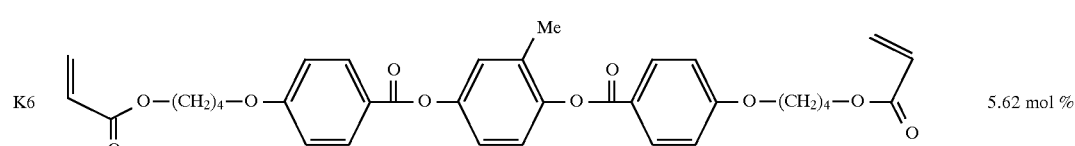 5.62 mol %
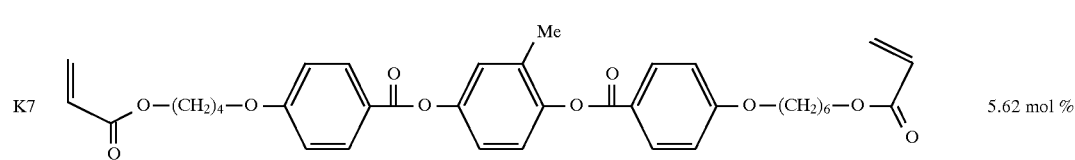 5.62 mol %

-continued

| ID | Structure | mol % |
|---|---|---|
| K8 | CH₂=CH−C(O)−O−(CH₂)₄−O−C₆H₄−C(O)−O−C₆H₃(Me)−O−C(O)−C₆H₄−O−(CH₂)₈−O−C(O)−CH=CH₂ | 5.62 mol % |
| K9 | CH₂=CH−C(O)−O−(CH₂)₆−O−C₆H₄−C(O)−O−C₆H₃(Me)−O−C(O)−C₆H₄−O−(CH₂)₂−O−C(O)−CH=CH₂ | 5.62 mol % |
| K10 | CH₂=CH−C(O)−O−(CH₂)₆−O−C₆H₄−C(O)−O−C₆H₃(Me)−O−C(O)−C₆H₄−O−(CH₂)₄−O−C(O)−CH=CH₂ | 5.62 mol % |
| K11 | CH₂=CH−C(O)−O−(CH₂)₆−O−C₆H₄−C(O)−O−C₆H₃(Me)−O−C(O)−C₆H₄−O−(CH₂)₆−O−C(O)−CH=CH₂ | 5.62 mol % |
| K12 | CH₂=CH−C(O)−O−(CH₂)₆−O−C₆H₄−C(O)−O−C₆H₃(Me)−O−C(O)−C₆H₄−O−(CH₂)₈−O−C(O)−CH=CH₂ | 5.62 mol % |
| K13 | CH₂=CH−C(O)−O−(CH₂)₈−O−C₆H₄−C(O)−O−C₆H₃(Me)−O−C(O)−C₆H₄−O−(CH₂)₂−O−C(O)−CH=CH₂ | 5.62 mol % |
| K14 | CH₂=CH−C(O)−O−(CH₂)₈−O−C₆H₄−C(O)−O−C₆H₃(Me)−O−C(O)−C₆H₄−O−(CH₂)₄−O−C(O)−CH=CH₂ | 5.62 mol % |
| K15 | CH₂=CH−C(O)−O−(CH₂)₈−O−C₆H₄−C(O)−O−C₆H₃(Me)−O−C(O)−C₆H₄−O−(CH₂)₆−O−C(O)−CH=CH₂ | 5.62 mol % |
| K16 | CH₂=CH−C(O)−O−(CH₂)₈−O−C₆H₄−C(O)−O−C₆H₃(Me)−O−C(O)−C₆H₄−O−(CH₂)₈−O−C(O)−CH=CH₂ | 5.62 mol % |
| K17 | CH₂=CH−C(O)−O−(CH₂)₂−O−C₆H₄−C(O)−O−C₆H₃(Cl)−O−C(O)−C₆H₄−O−(CH₂)₂−O−C(O)−CH=CH₂ | 0.63 mol % |

-continued

| | | |
|---|---|---|
| K18 | CH2=CH-C(=O)-O-(CH2)2-O-C6H4-C(=O)-O-C6H3(Cl)-O-C(=O)-C6H4-O-(CH2)4-O-C(=O)-CH=CH2 | 0.63 mol % |
| K19 | CH2=CH-C(=O)-O-(CH2)2-O-C6H4-C(=O)-O-C6H3(Cl)-O-C(=O)-C6H4-O-(CH2)6-O-C(=O)-CH=CH2 | 0.63 mol % |
| K20 | CH2=CH-C(=O)-O-(CH2)2-O-C6H4-C(=O)-O-C6H3(Cl)-O-C(=O)-C6H4-O-(CH2)8-O-C(=O)-CH=CH2 | 0.63 mol % |
| K21 | CH2=CH-C(=O)-O-(CH2)4-O-C6H4-C(=O)-O-C6H3(Cl)-O-C(=O)-C6H4-O-(CH2)2-O-C(=O)-CH=CH2 | 0.63 mol % |
| K22 | CH2=CH-C(=O)-O-(CH2)4-O-C6H4-C(=O)-O-C6H3(Cl)-O-C(=O)-C6H4-O-(CH2)4-O-C(=O)-CH=CH2 | 0.63 mol % |
| K23 | CH2=CH-C(=O)-O-(CH2)4-O-C6H4-C(=O)-O-C6H3(Cl)-O-C(=O)-C6H4-O-(CH2)6-O-C(=O)-CH=CH2 | 0.63 mol % |
| K24 | CH2=CH-C(=O)-O-(CH2)4-O-C6H4-C(=O)-O-C6H3(Cl)-O-C(=O)-C6H4-O-(CH2)8-O-C(=O)-CH=CH2 | 0.63 mol % |
| K25 | CH2=CH-C(=O)-O-(CH2)6-O-C6H4-C(=O)-O-C6H3(Cl)-O-C(=O)-C6H4-O-(CH2)2-O-C(=O)-CH=CH2 | 0.63 mol % |
| K26 | CH2=CH-C(=O)-O-(CH2)6-O-C6H4-C(=O)-O-C6H3(Cl)-O-C(=O)-C6H4-O-(CH2)4-O-C(=O)-CH=CH2 | 0.63 mol % |
| K27 | CH2=CH-C(=O)-O-(CH2)6-O-C6H4-C(=O)-O-C6H3(Cl)-O-C(=O)-C6H4-O-(CH2)6-O-C(=O)-CH=CH2 | 0.63 mol % |

-continued
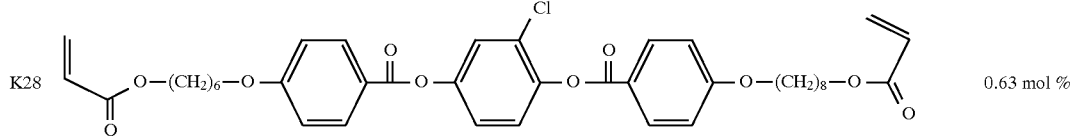 K28  0.63 mol %
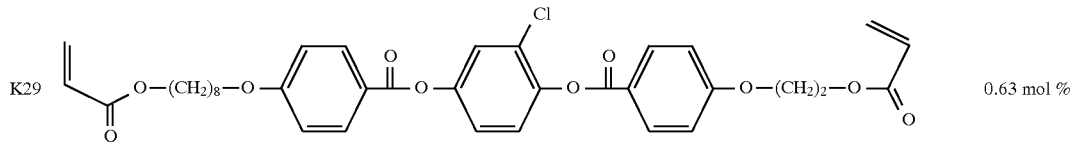 K29  0.63 mol %
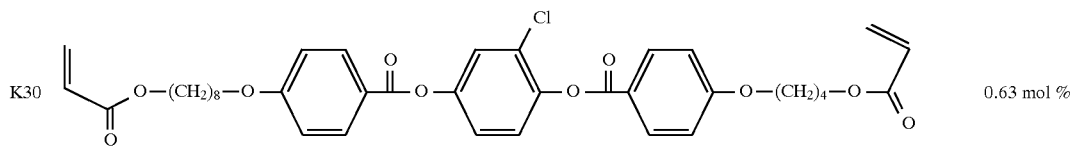 K30  0.63 mol %
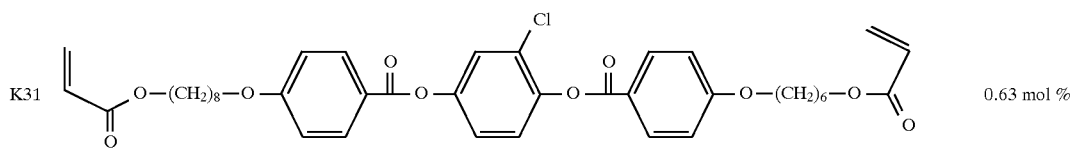 K31  0.63 mol %
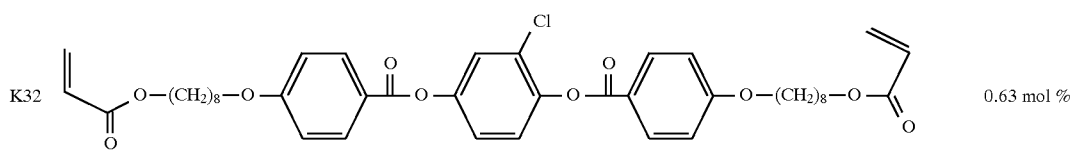 K32  0.63 mol %
EXAMPLE 97
Mixture 45:
K1 to K32 as K1 to K32 in mixture 44, each in a concentration of 5.34 mol % for K1 to K16 and 0.59 mol % for K17–K32
K33 as K10 in mixture 26 in a concentration of 5.0 mol %
Phase behavior: C<25N* 66–68 I
Color=red
EXAMPLE 98
Mixture 44:
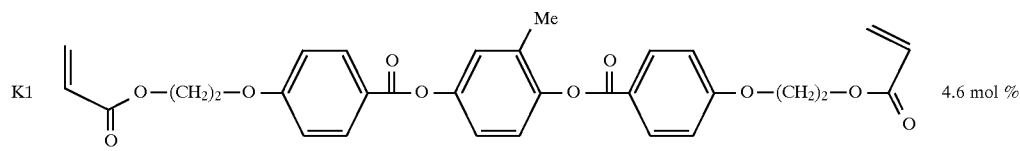 K1  4.6 mol %
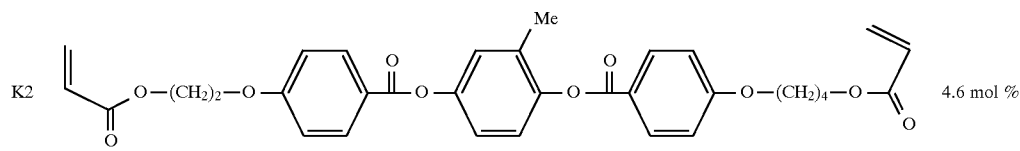 K2  4.6 mol %
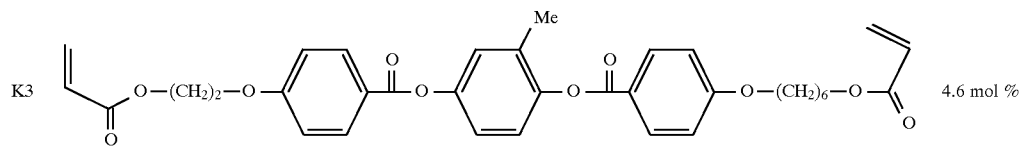 K3  4.6 mol %
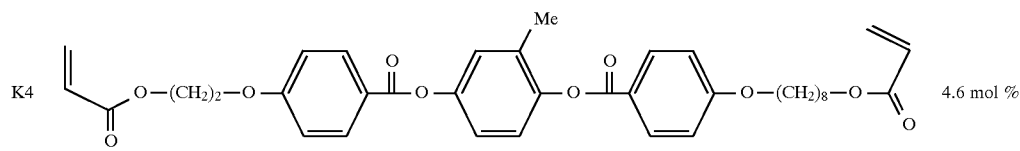 K4  4.6 mol %

-continued
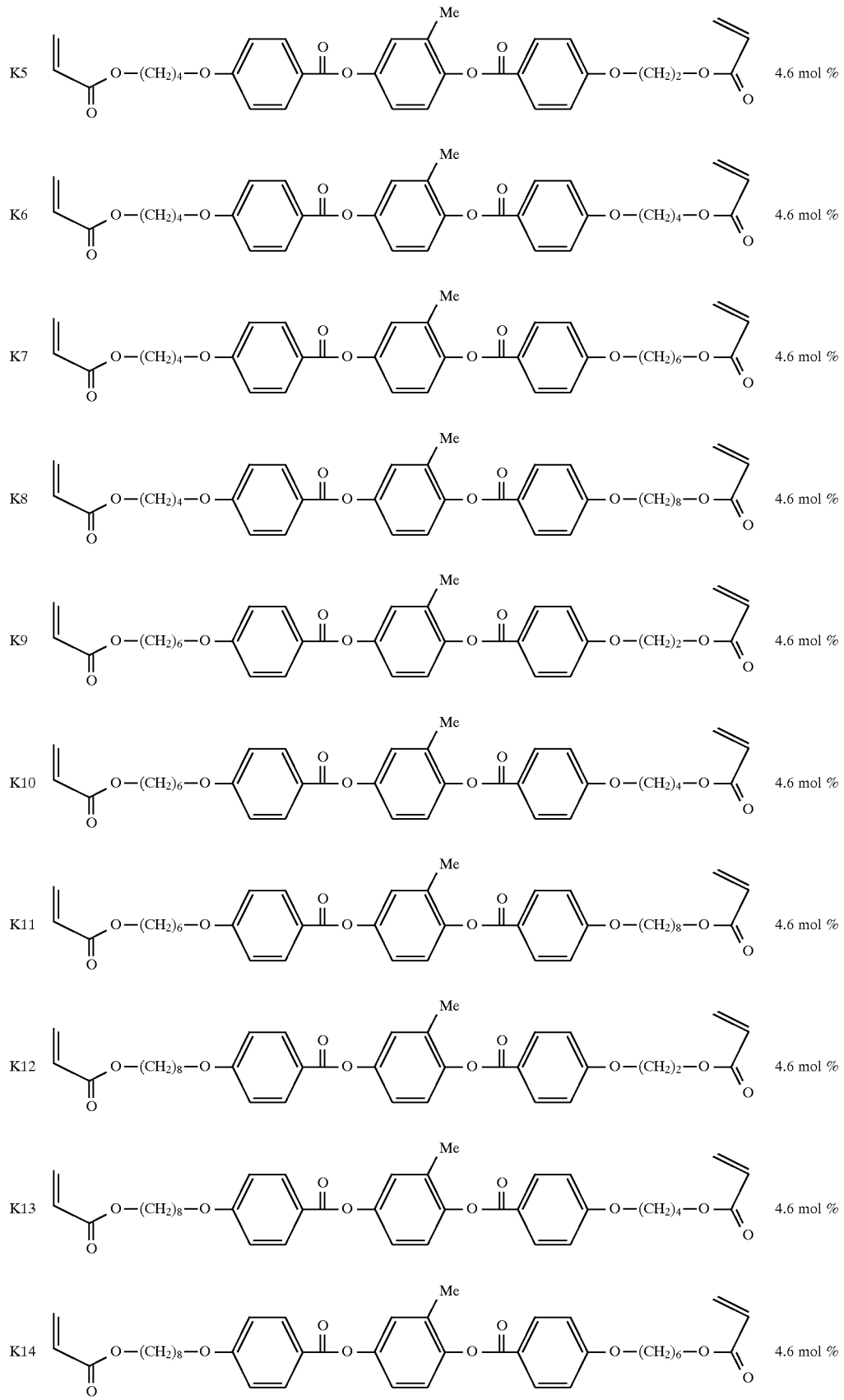

-continued
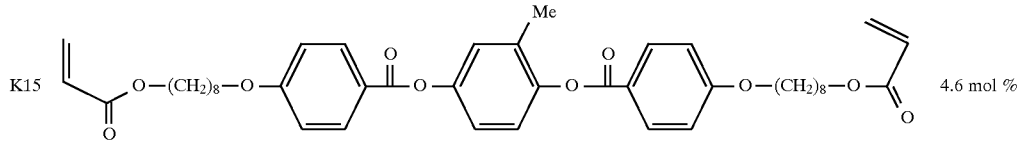 K15    4.6 mol %
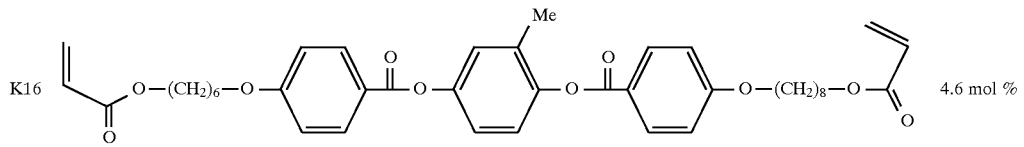 K16    4.6 mol %
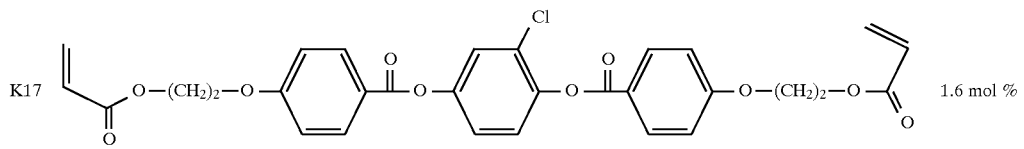 K17    1.6 mol %
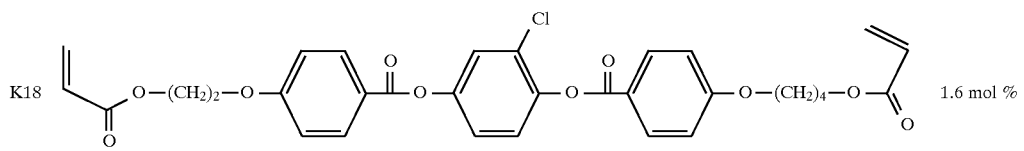 K18    1.6 mol %
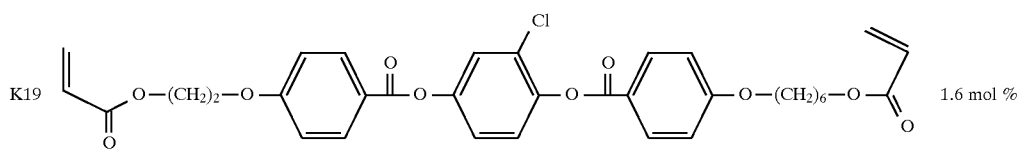 K19    1.6 mol %
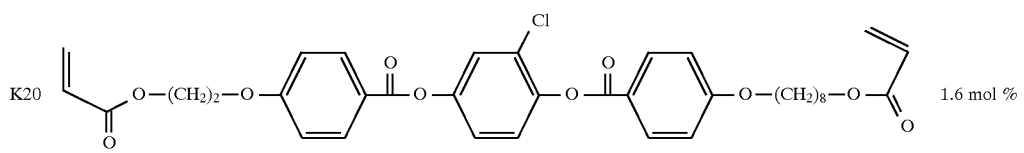 K20    1.6 mol %
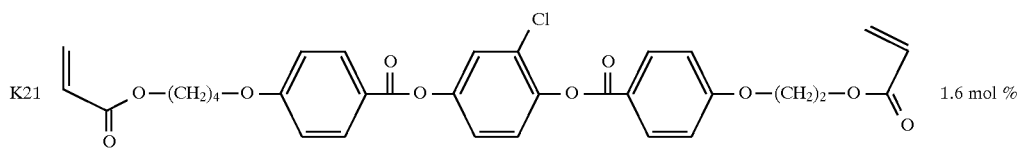 K21    1.6 mol %
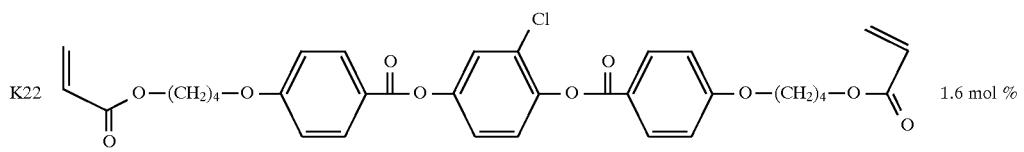 K22    1.6 mol %
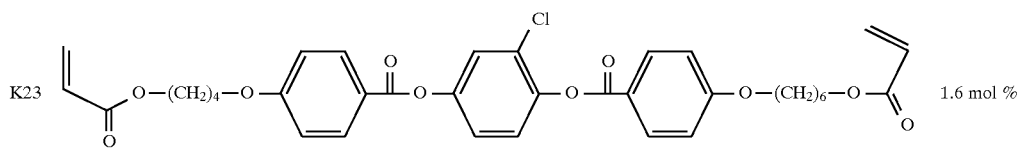 K23    1.6 mol %
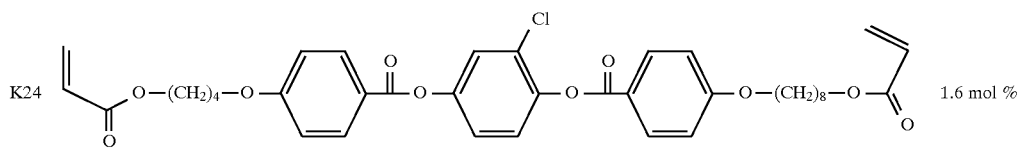 K24    1.6 mol %

-continued
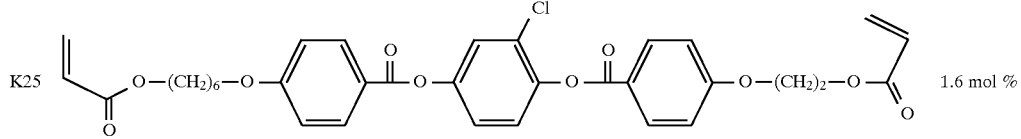 1.6 mol %
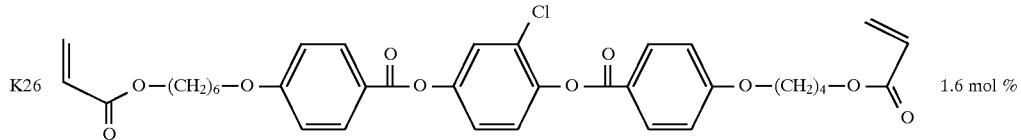 1.6 mol %
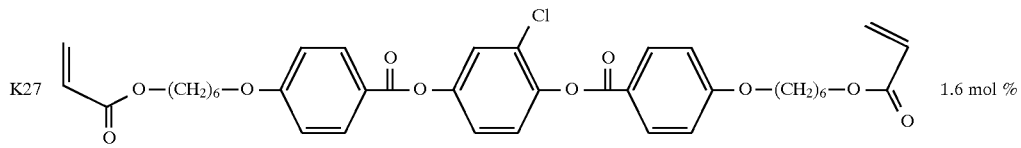 1.6 mol %
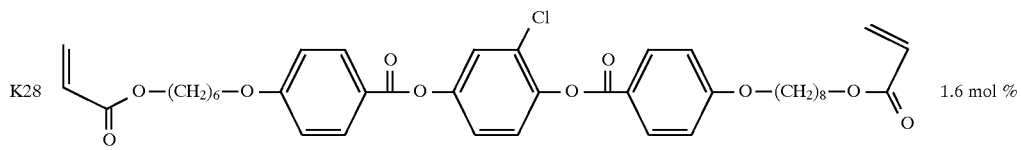 1.6 mol %
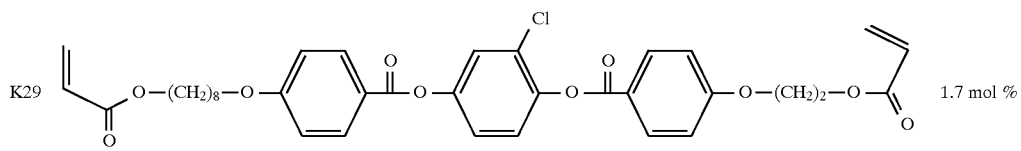 1.7 mol %
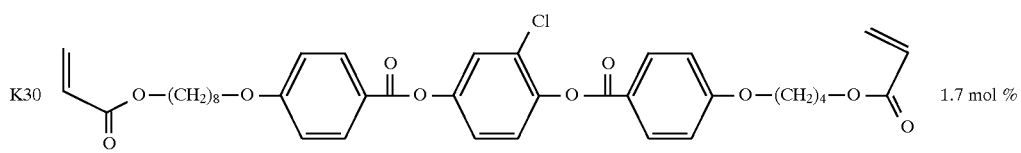 1.7 mol %
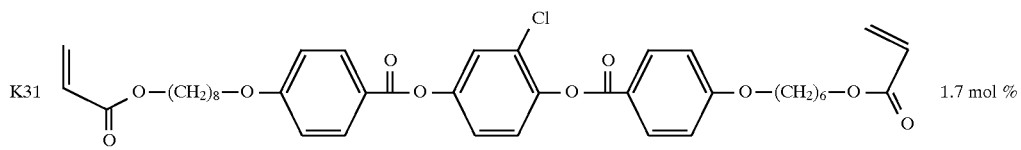 1.7 mol %
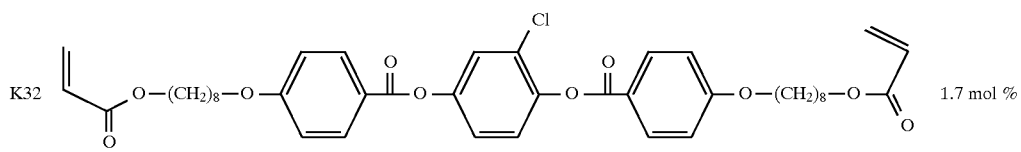 1.7 mol %
Phase behavior: C<25N 66–69 I
Color=red
EXAMPLE 99
Mixture 47:
K1 to K32 as in mixture 46, each in a concentration of 4.5 mol % for K1 to K16 and 1.5 mol % for K17 to K32
K33 as K10 in mixture 26 in a concentration of 4 mol %
Phase behavior: C<25N* 67 I
EXAMPLE 100
Mixture 48:
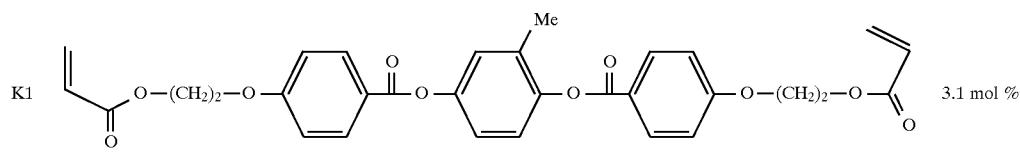 3.1 mol %

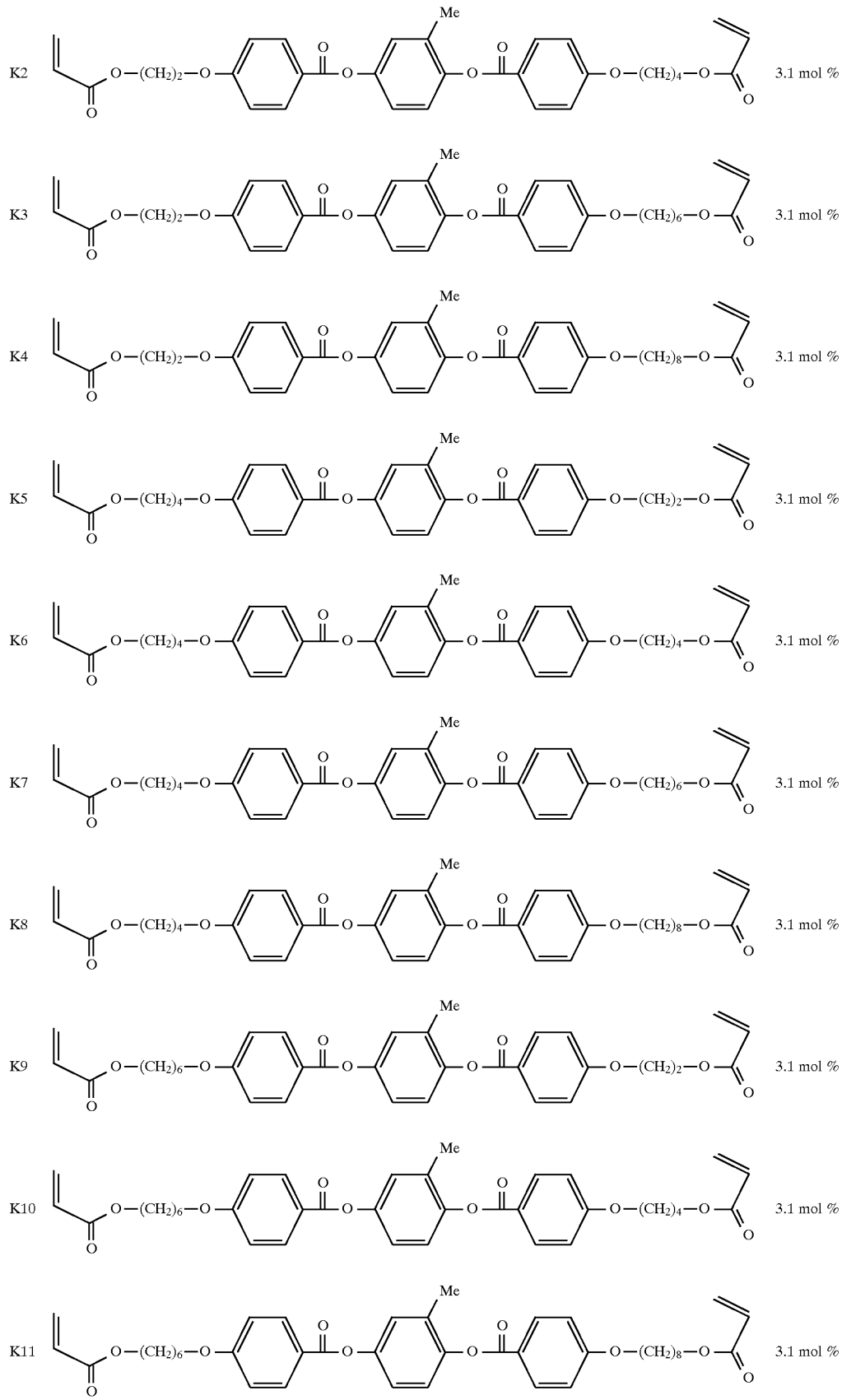

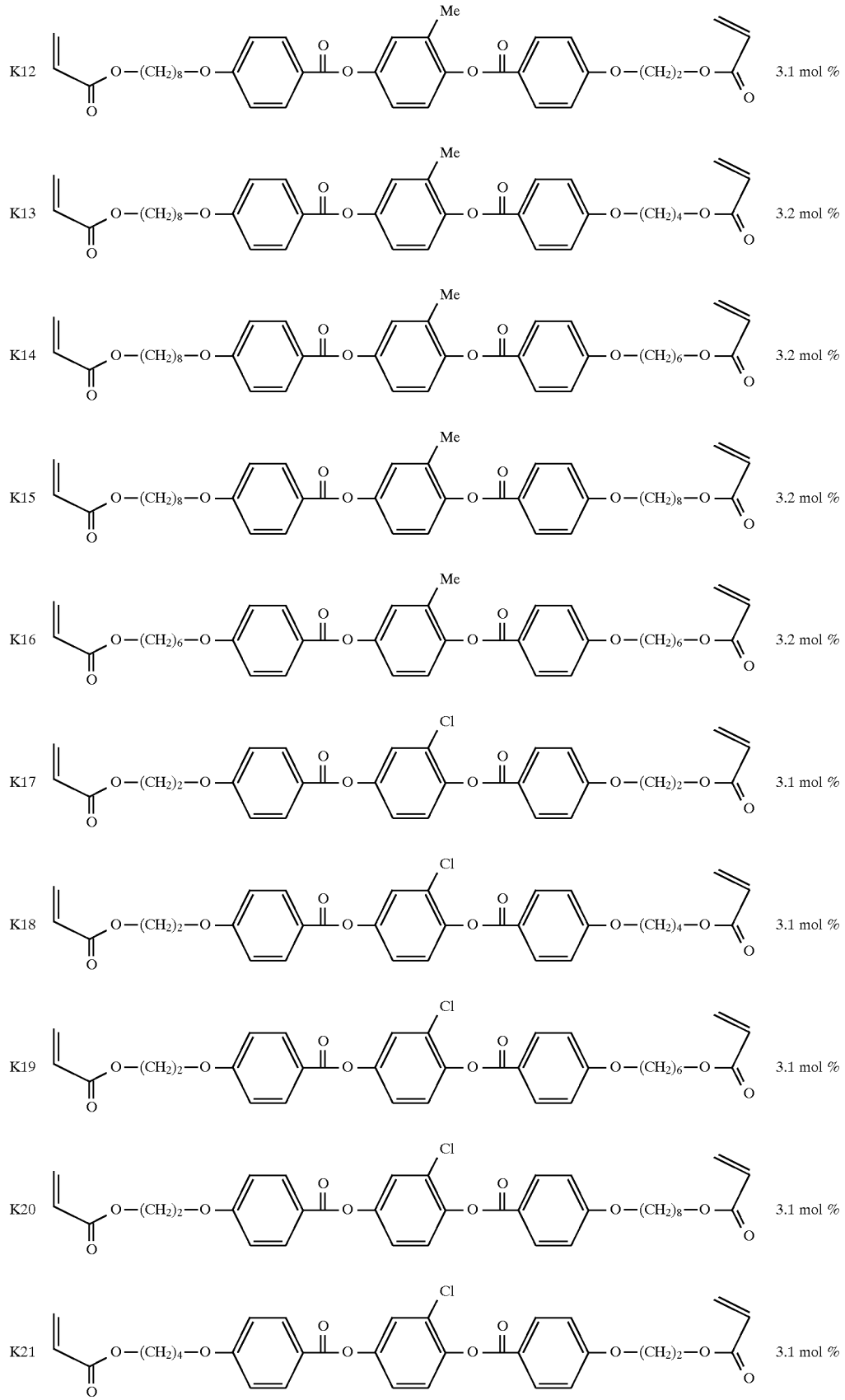

K22 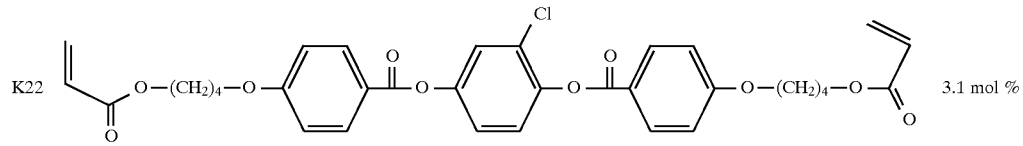 3.1 mol %
K23 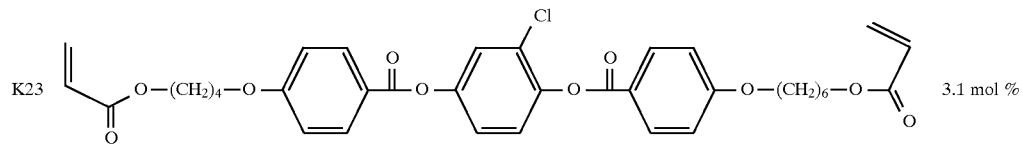 3.1 mol %
K24 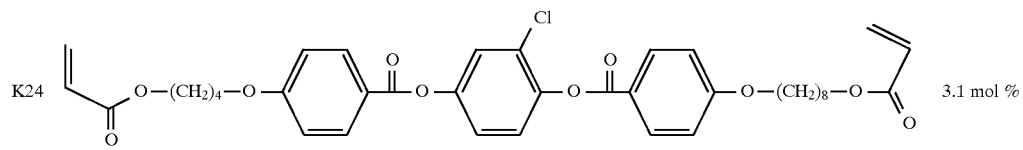 3.1 mol %
K25 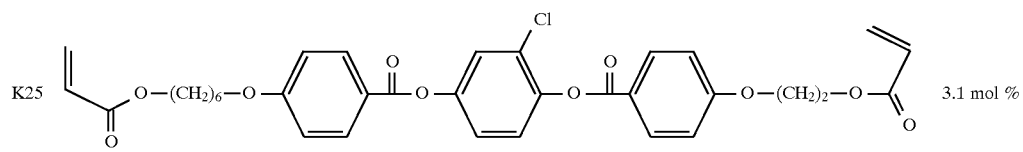 3.1 mol %
K26 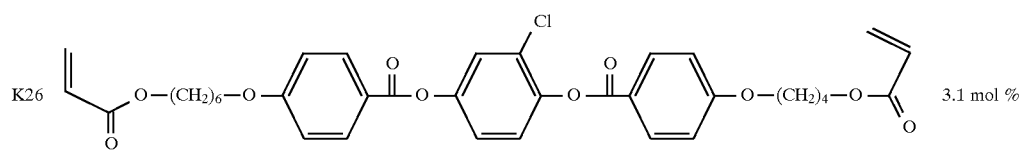 3.1 mol %
K27 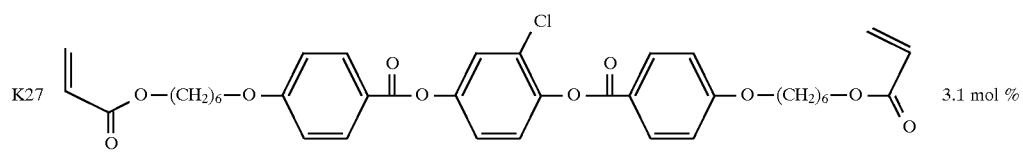 3.1 mol %
K28 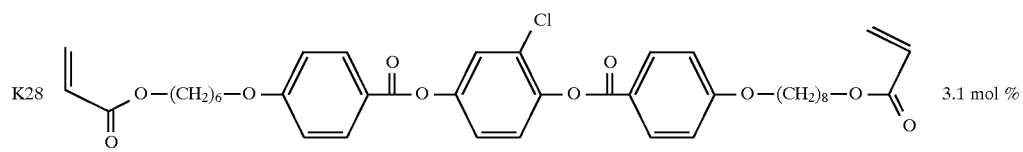 3.1 mol %
K29 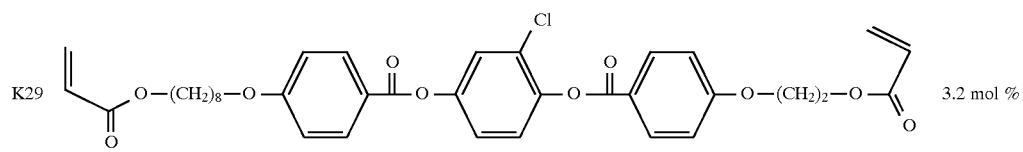 3.2 mol %
K30 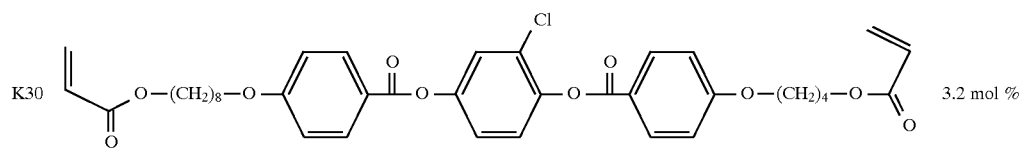 3.2 mol %
K31 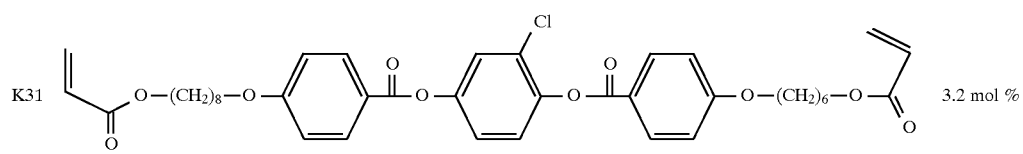 3.2 mol %

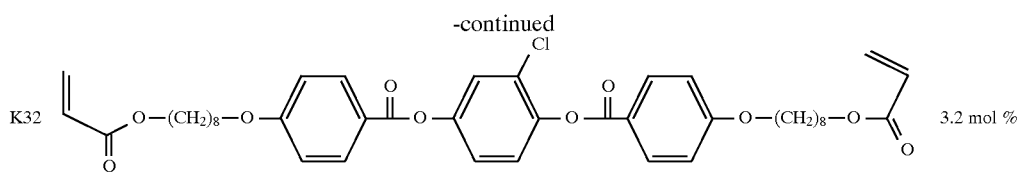
Phase behavior: C<25N 66–69 I
EXAMPLE 101
Mixture 49:
K1 to K32 as in mixture 48, each in a concentration of 3.0 mol %
K33 as K10 in mixture 26 in a concentration of 5 mol %
Phase behavior: C<25N* 62–66 I
EXAMPLE 102
Mixture 50:
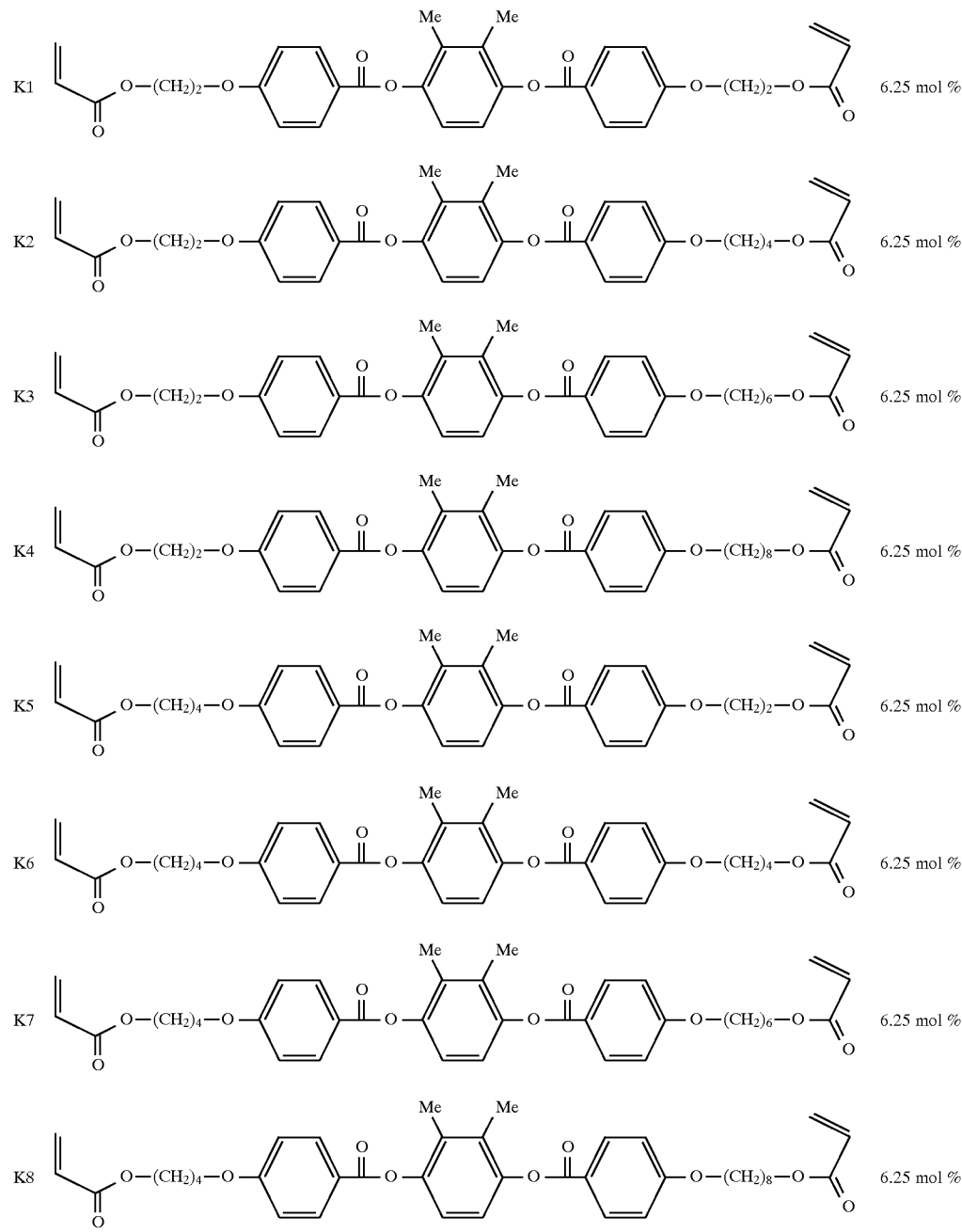

-continued

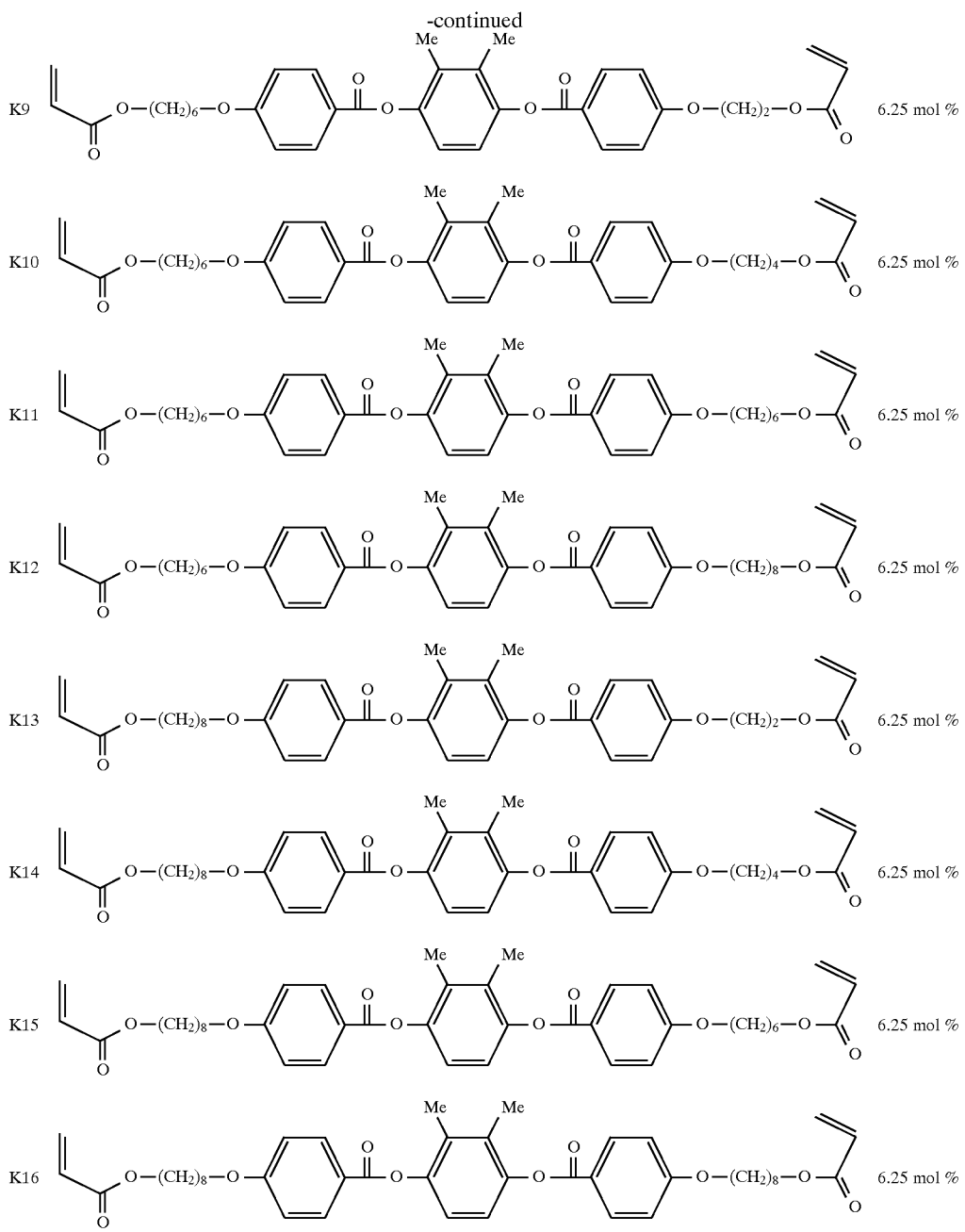

Phase behavior: C 58N 93 I

EXAMPLE 103

Mixture 51:

K1 to K16 as K1 to K16 in mixture 50, each in a concentration of 5.94 mol %

K17 as K10 in mixture 26 in a concentration of 5 mol %

Phase behavior: <56N* 91–94 I

EXAMPLE 104

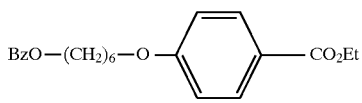

a) Ethyl 4-[ω-benzyloxyhexoxy]benzoate 16.6 g of ethyl 4-hydroxybenzoate are added slowly at 20° C. to a suspension of 4.8 g of sodium hydride (60% dispersion in oil) until the evolution of $H_2$ has subsided. The mixture is then stirred for a further one hour at room temperature, and 19.9 g of 6-benzyloxy-1-chlorohexane are added. The mixture is refluxed for 16 hours, the resultant precipitate is filtered off, and the solvent is removed. Recrystallization from toluene gives 15.2 g of the above compound. NMR, MS and IR agree with the structure.

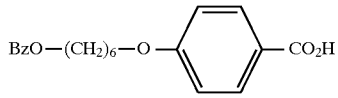

b) 4-[ω-Benzyloxyhexoxy]benzoic acid 2 equivalents of KOH are added to a solution of 10 g of the product from a) in 300 ml of ethanol, and the mixture is refluxed for 4 hours. The reaction mixture is then poured into water and acidified using conc. hydrochloric acid. The resultant precipitate is filtered off and dried under reduced pressure overnight at 50° C., giving 8.5 g of the above compound. NMR, MS and IR agree with the structure.

c) 1,4-[4'-(ω-Benzyloxyhexoxy]benzoyloxy]-(4'-(ω-benzyloxybutoxy)benzoyloxy]benzene 4 g of 4-[ω-benzyloxyhexoxy]benzoic acid, 3.9 g of 4-[4-benzyloxybutoxy]benzoic acid and 2 g of hydroquinone are reacted as described in Example 1, giving 7.2 g of the above compound. NMR, IR and MS agree with the structure.

d) 1-[4'-(ω-Hydroxyhexoxy)benzoyloxy]-4-[4"-(ω-hydroxybutoxy)-benzoyloxy]benzene 12 g of 1-[4'-(ω-benzyloxyhexoxy)benzoyloxy]-4-[4"-(ω-benzyloxybutoxy) benzoyloxy]benzene are dissolved in 200 ml of ethanol, 2 g of Pd/C (10%) are added, and the mixture is stirred at room temperature for 6 hours under a hydrogen atmosphere until the take-up of hydrogen is complete. The catalyst is then filtered off, the solvent is removed, and the residue is recrystallized from toluene, giving 8.5 g of the above compound. NMR, IR and MS agree with the structure.

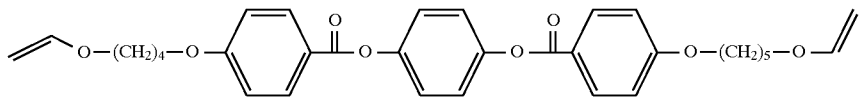

e) 1-[4'-(ω-Vinyloxyhexoxy)benzoyloxy]-4-[4"-(ω-vinyloxybutoxy)-benzoyloxy]benzene 8.5 g of the product d) together with 1.5 g of Hg(OAc)$_2$ are dissolved in 500 ml of ethyl vinyl ether, and the mixture is refluxed for 24 hours. 5 g of $K_2CO_3$ are then added, and the excess ethyl vinyl ether is removed by distillation. The residue is filtered, and the $K_2CO_3$ is washed with petroleum ether. The filtrate and washings are evaporated, and the residue is recrystallized from petroleum ether/ethyl acetate (9:1), giving 8.1 g of the above compound. NMR, MS and IR agree with the structure.

EXAMPLES
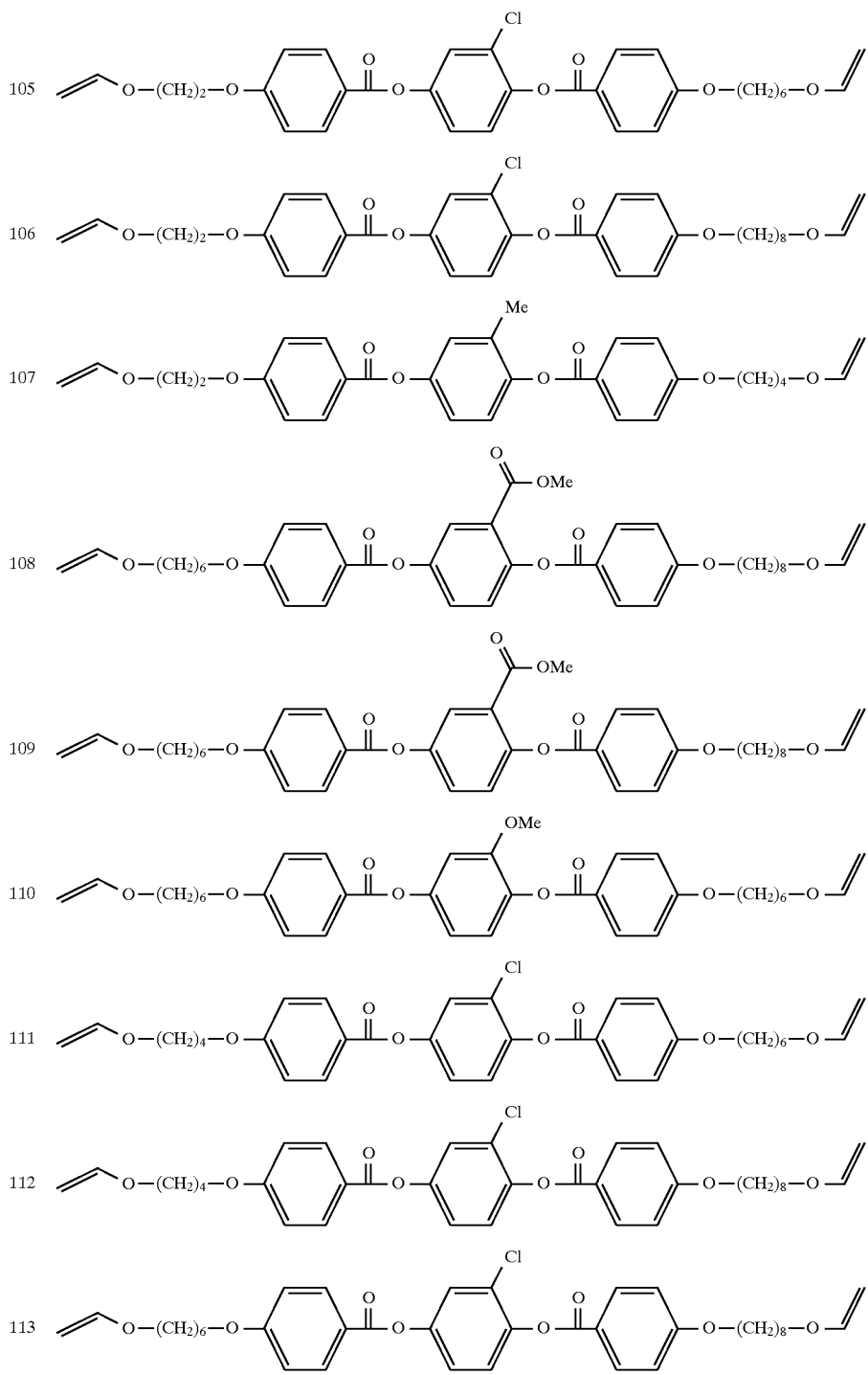
EXAMPLE 114
Mixture 30:
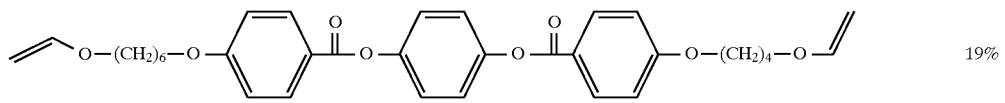  19%

-continued
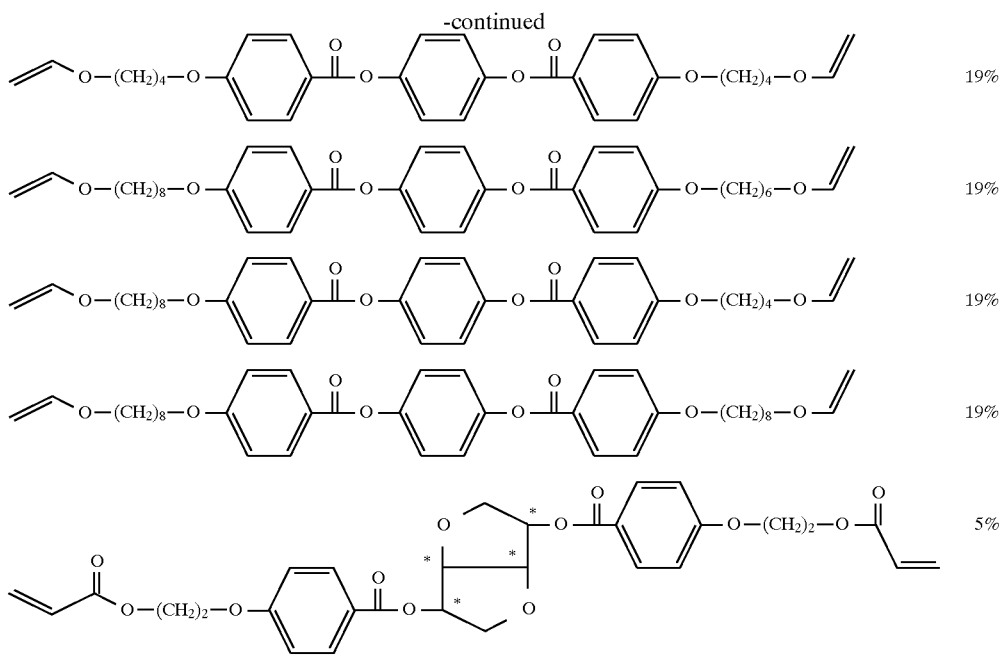
19%
19%
19%
19%
5%
Color: green to red
EXAMPLE 115
Mixture 31:
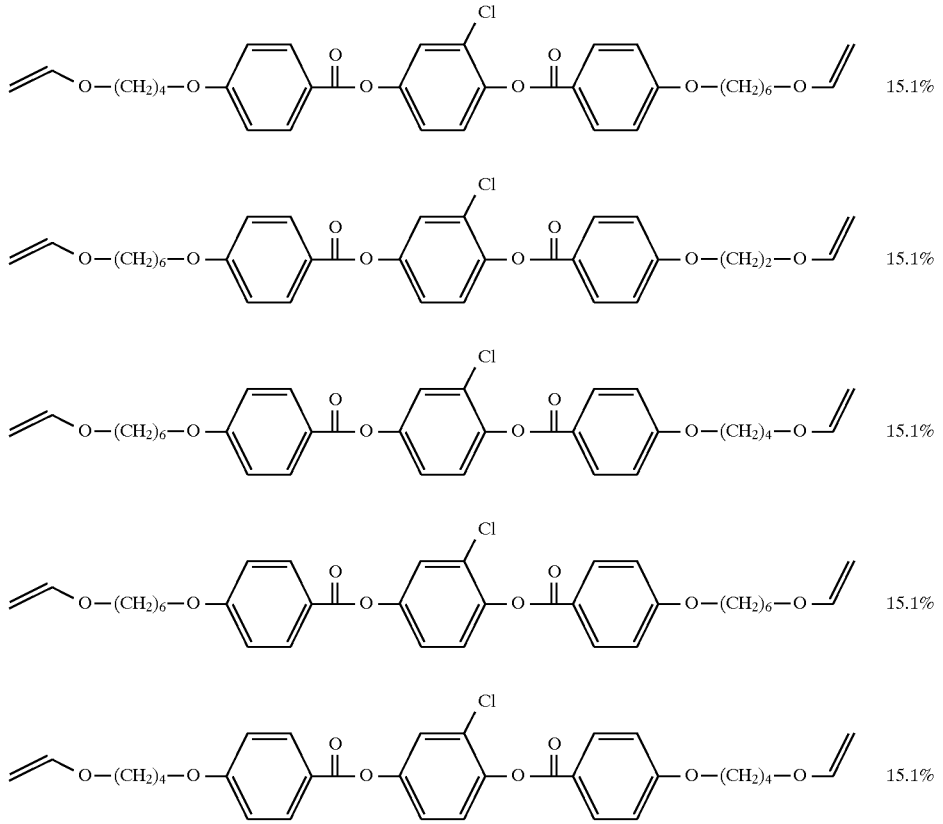
15.1%
15.1%
15.1%
15.1%
15.1%

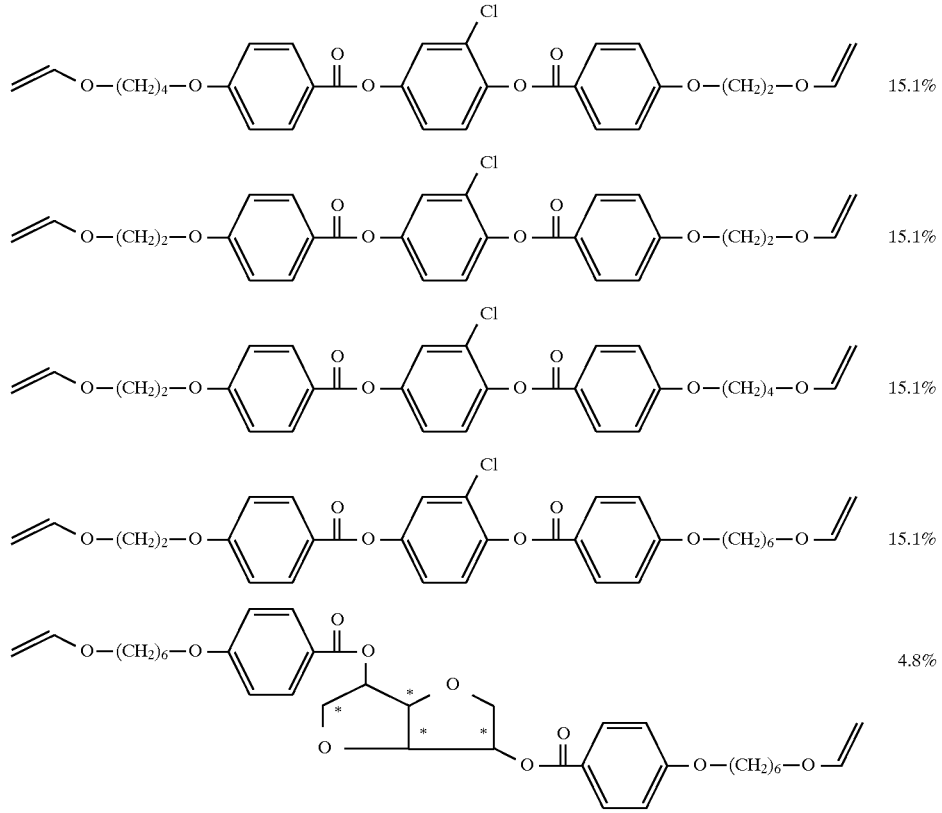
Phase behavior: ch 75 I
Color: red-green
EXAMPLE 116
Mixture 32:
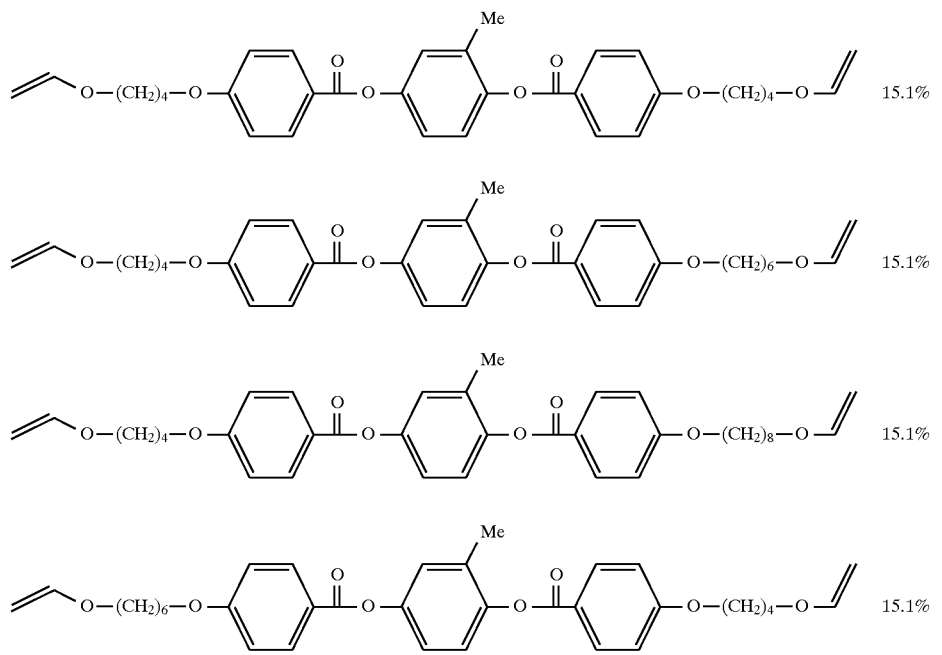

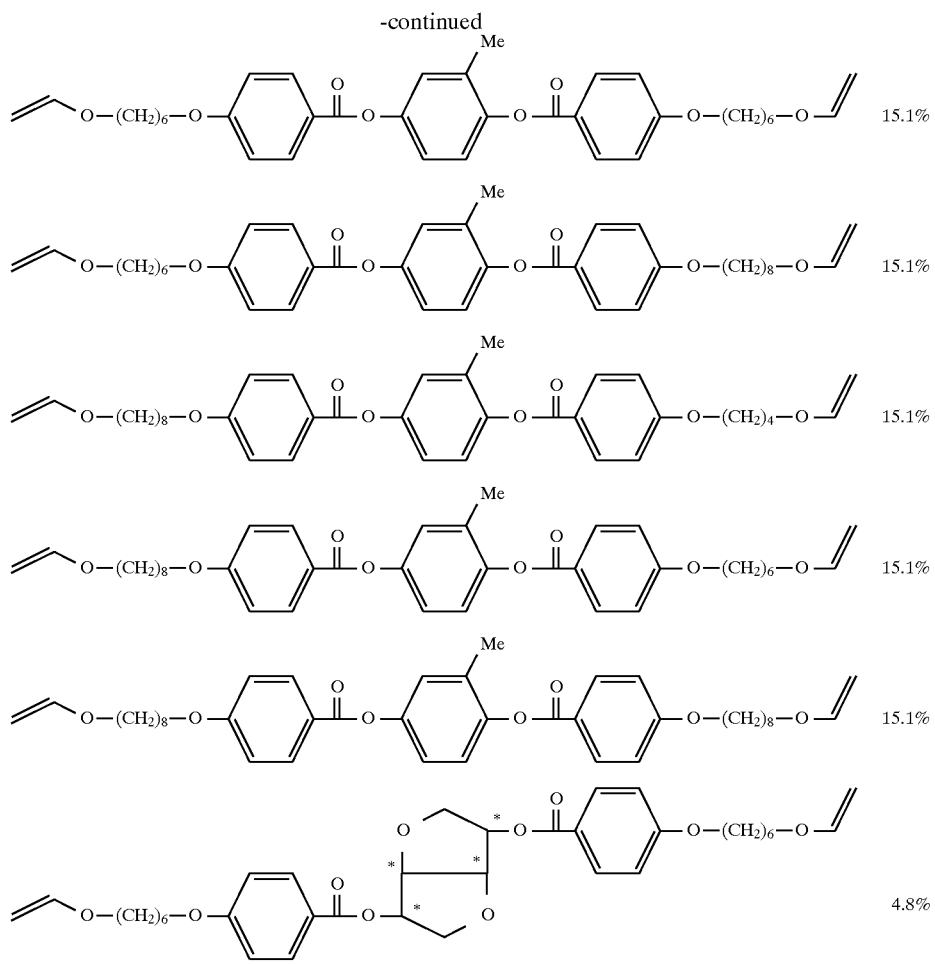

15.1%

15.1%

15.1%

15.1%

15.1%

4.8%

Phase behavior: ch 85 I
Color: red-green

EXAMPLE 117

Synthesis of

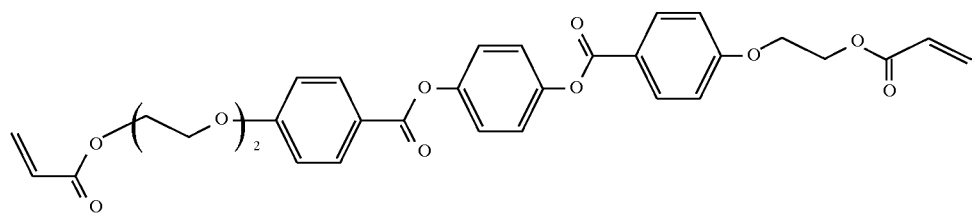

a. Etherification of ethyl 4-hydroxybenzoate using diethylene glycol 3.65 g (0.022 mol) of ethyl 4-hydroxybenzoate together with 11.66 g (0.11 mol) of diethylene glycol are dissolved in 35 ml of abs. tetrahydrofuran, and 8.7 g (0.033 mol) of diethyl azodicarboxylate are added. The reaction mixture is stirred at RT for 24 hours. The mixture is subsequently evaporated on a rotary evaporator, and the residue is purified by column chromatography (silica gel, eluent: toluene/ethyl acetate 5:1).

Yield: 4.36 g, 78%.

b. Preparation of 4-(diethylene glycoloxy)benzoic acid 4.36 g (0.017 mol) of ethyl 4-(2-diethylene glycoloxy) benzoate are dissolved in 80 ml of ethanol, and 1.46 g (0.026 mol) of KOH are added. The mixture is refluxed for 3 hours, the solution is then acidified using conc. hydrochloric acid, ethyl acetate is added, and the resulting precipitate is filtered off with suction. The residue is discarded, and evaporation of the filtrate gives the desired product.

Yield: 4.7 g, 98%.

The further steps in the preparation of the compound of Example 117 correspond to those of Example 1.

| Ex. | Z¹—Y¹— | A¹ | T¹ | T² | T³ | A² | —Y²—Z² |
|---|---|---|---|---|---|---|---|
| 118 | $CH_2=CH-C(=O)-O-$ | $-[CH_2-CH_2-O]_3-$ | $-C_6H_4-C(=O)-O-$ | $-C_6H_4-$ | $-O-C(=O)-C_6H_4-$ | $-O-CH_2-CH_2-$ | $-O-C(=O)-CH=CH_2$ |
| 119 | $CH_2=CH-C(=O)-O-$ | $+CH_2-CH_2-O+_3$ | $-C_6H_4-C(=O)-O-$ | $-C_6H_4-$ | $-O-C(=O)-C_6H_4-$ | $+O-CH_2-CH_2+_2$ | $-O-C(=O)-CH=CH_2$ |
| 120 | $CH_2=CH-C(=O)-O-$ | $+CH_2-CH_2-O+_2$ | $-C_6H_4-C(=O)-O-$ | $-C_6H_4-$ | $-O-C(=O)-C_6H_4-$ | $+O-CH_2-CH_2+_2$ | $-O-C(=O)-CH=CH_2$ |
| 121 | $CH_2=CH-C(=O)-O-$ | $+CH_2-CH_2-O+_3$ | $-C_6H_4-C(=O)-O-$ | $-C_6H_4-$ | $-O-C(=O)-C_6H_4-$ | $+O-CH_2-CH_2+_3$ | $-O-C(=O)-CH=CH_2$ |
| 122 | $CH_2=CH-C(=O)-O-$ | $-CH_2-CH_2-O$ | $-C_6H_4-C(=O)-O-$ | $-C_6H_3(Cl)-$ | $-O-C(=O)-C_6H_4-$ | $+O-CH_2-CH_2+_2$ | $-O-C(=O)-CH=CH_2$ |
| 123 | $CH_2=CH-C(=O)-O-$ | $-CH_2-CH_2-O$ | $-C_6H_4-C(=O)-O-$ | $-C_6H_3(Cl)-$ | $-O-C(=O)-C_6H_4-$ | $+O-CH_2-CH_2+_3$ | $-O-C(=O)-CH=CH_2$ |
| 124 | $CH_2=CH-C(=O)-O-$ | $+CH_2-CH_2-O+_2$ | $-C_6H_4-C(=O)-O-$ | $-C_6H_3(Cl)-$ | $-O-C(=O)-C_6H_4-$ | $-O-CH_2-CH_2-$ | $-O-C(=O)-CH=CH_2$ |
| 125 | $CH_2=CH-C(=O)-O-$ | $+CH_2-CH_2-O+_2$ | $-C_6H_4-C(=O)-O-$ | $-C_6H_3(Cl)-$ | $-O-C(=O)-C_6H_4-$ | $+O-CH_2-CH_2+_3$ | $-O-C(=O)-CH=CH_2$ |
| 126 | $CH_2=CH-C(=O)-O-$ | $+CH_2-CH_2-O+_3$ | $-C_6H_4-C(=O)-O-$ | $-C_6H_3(Cl)-$ | $-O-C(=O)-C_6H_4-$ | $O-CH_2-CH_2$ | $-O-C(=O)-CH=CH_2$ |
| 127 | $CH_2=CH-C(=O)-O-$ | $+CH_2-CH_2-O+_3$ | $-C_6H_4-C(=O)-O-$ | $-C_6H_3(Cl)-$ | $-O-C(=O)-C_6H_4-$ | $+O-CH_2-CH_2+_2$ | $-O-C(=O)-CH=CH_2$ |
| 128 | $CH_2=CH-C(=O)-O-$ | $+CH_2-CH_2-O+_2$ | $-C_6H_4-C(=O)-O-$ | $-C_6H_3(Cl)-$ | $-O-C(=O)-C_6H_4-$ | $+O-CH_2-CH_2+_2$ | $-O-C(=O)-CH=CH_2$ |
| 129 | $CH_2=CH-C(=O)-O-$ | $+CH_2-CH_2-O+_3$ | $-C_6H_4-C(=O)-O-$ | $-C_6H_3(Cl)-$ | $-C_6H_4-C(=O)-O-$ | $+O-CH_2-CH_2+_3$ | $-O-C(=O)-CH=CH_2$ |
| 130 | $CH_2=CH-C(=O)-O-$ | $+CH_2-CH_2-O+_3$ | $-C_6H_3(CH_3)-C(=O)-O-$ | $-C_6H_3(Cl)-$ | $-C_6H_4-C(=O)-O-$ | $+O-CH_2-CH_2+_3$ | $-O-C(=O)-CH=CH_2$ |
| 131 | $CH_2=CH-C(=O)-O-$ | $+CH_2-CH_2-O+_3$ | $-C_6H_4-C(=O)-O-$ | $-C_6H_3(Cl)-$ | $-C_6H_4-C(=O)-O-$ | $+O-CH_2-CH_2+_3$ | $-O-CH=CH_2$ |

EXAMPLE 132
Mixture 33:
K1; concentration 25 mol %
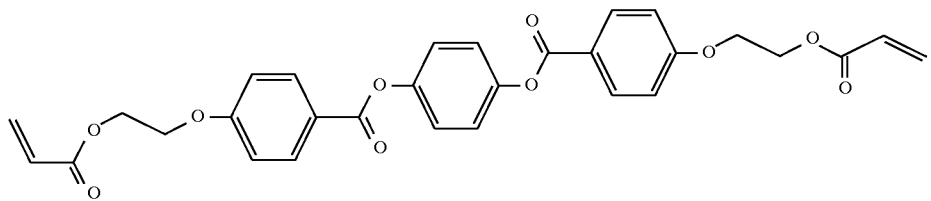
K2; concentration 45 mol %
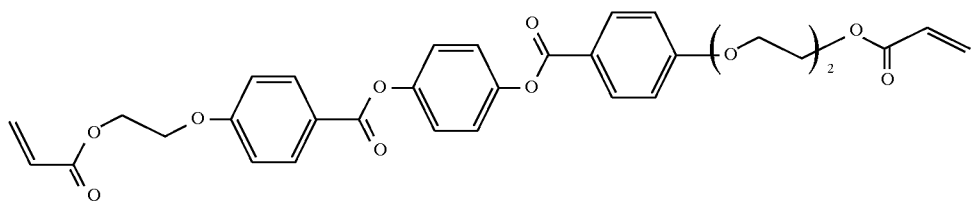
K3; concentration 5 mol %
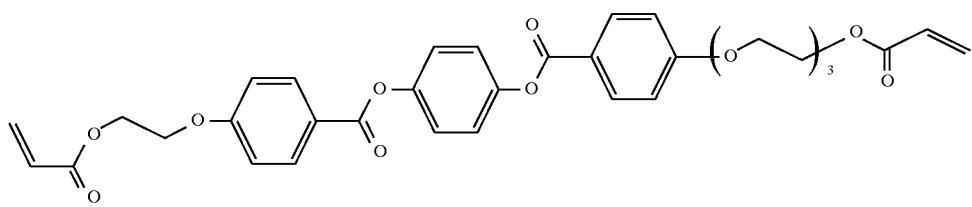
K4; concentration 20.25 mol %
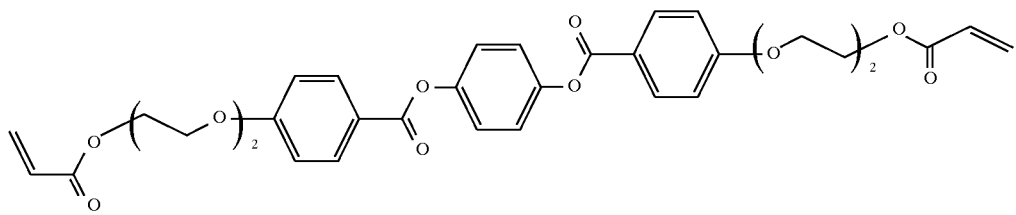
K5; concentration 4.5 mol %
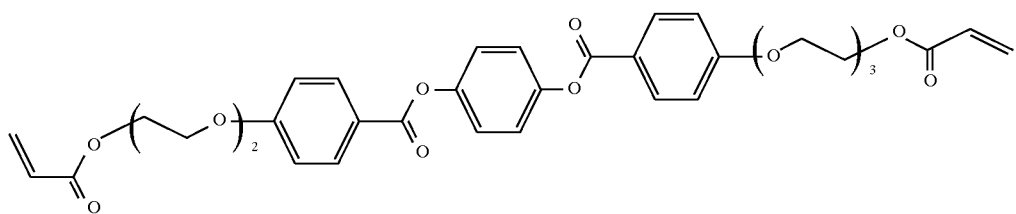

K6; concentration 0.25 mol %

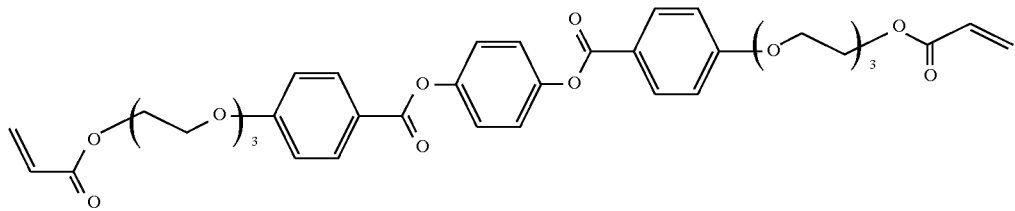

Phase behavior: S 45 N 83 I

EXAMPLE 133

Mixture 34:
  K1 as K1 of Example 132; concentration 23.75 mol %
  K2 as K2 of Example 132; concentration 42.75 mol %
  K3 as K3 of Example 132; concentration 4.75 mol %
  K4 as K4 of Example 132; concentration 19.2375 mol %
  K5 as K5 of Example 132; concentration 4.275 mol %
  K6 as K6 of Example 132; concentration 0.002375 mol %
  K7; concentration 5 mol %

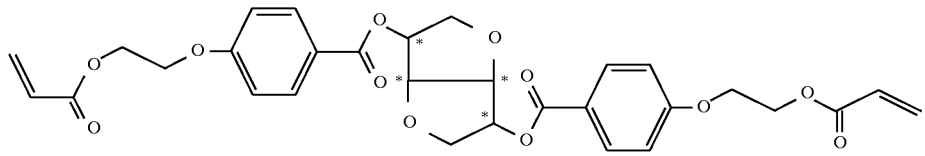

Phase behavior: S 41 Ch 81 I
Color: red/green

EXAMPLE 134

Mixture 35:
  K1 as K1 of Example 132; concentration 23.25 mol %
  K2 as K2 of Example 132; concentration 41.85 mol %
  K3 as K3 of Example 132; concentration 4.65 mol %
  K4 as K4 of Example 132; concentration 18.8325 mol %
  K5 as K5 of Example 132; concentration 4.185 mol %
  K6 as K6 of Example 132; concentration 0.002325 mol %
  K7 as K7 of Example 133; concentration 7 mol %
Phase behavior: S 40 Ch 80 I
Color: green/blue

EXAMPLE 135

Mixture 36:
  K1; concentration 25 mol %

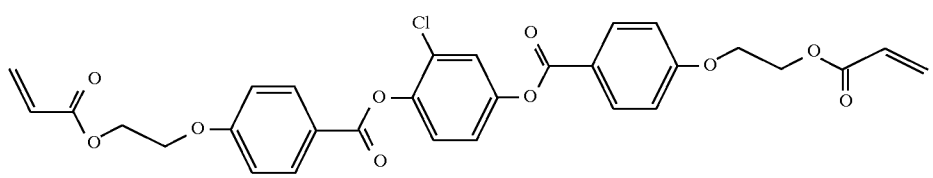

K2; concentration 22.5 mol %
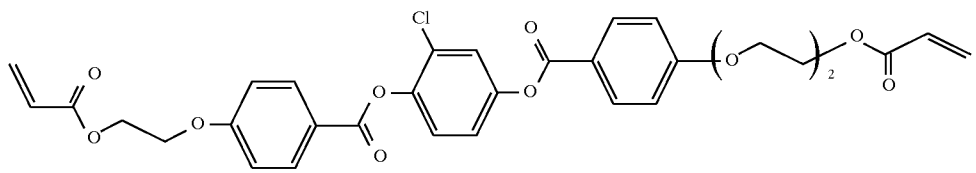
K3; concentration 2.5 mol %
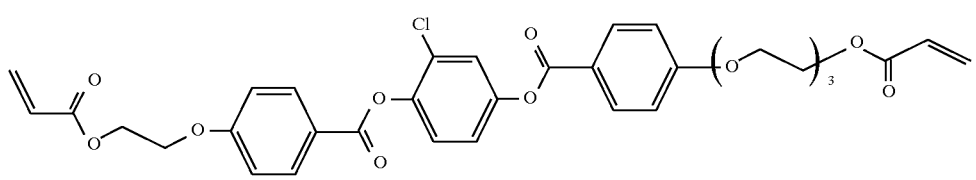
K4; concentration 22.5 mol %
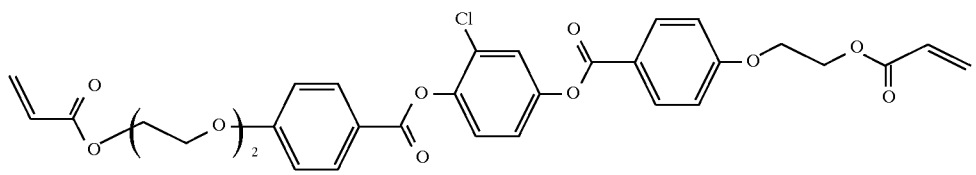
K5; concentration 20.25 mol %
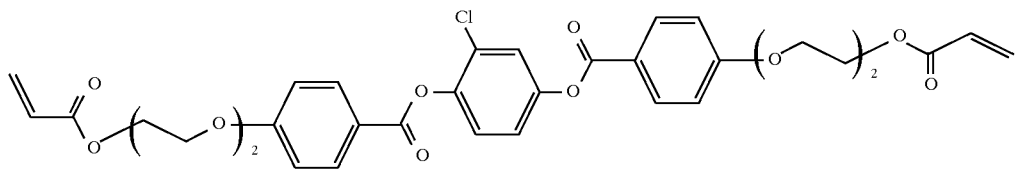
K6; concentration 2.25 mol %
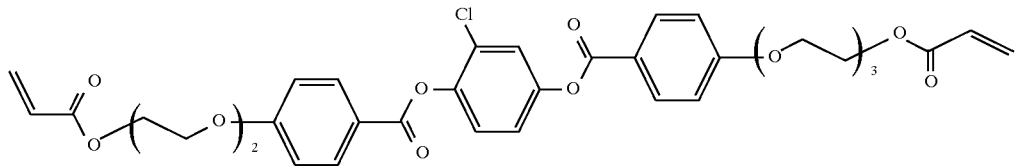
K7; concentration 2.5 mol %
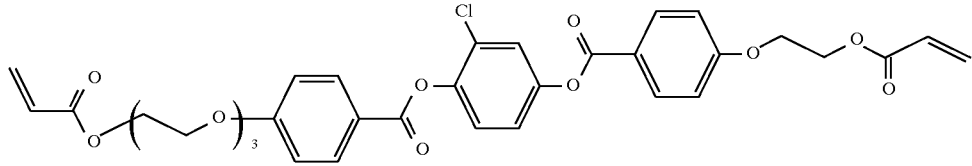
K8; concentration 2.25 mol %

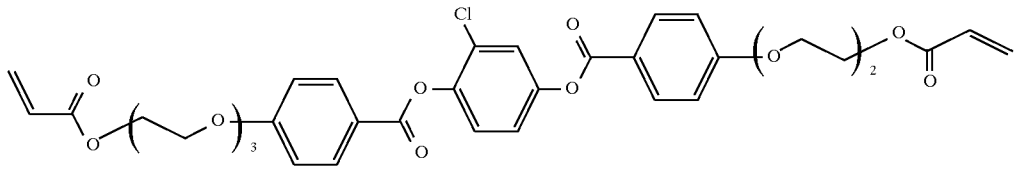

K9; concentration 0.25 mol %

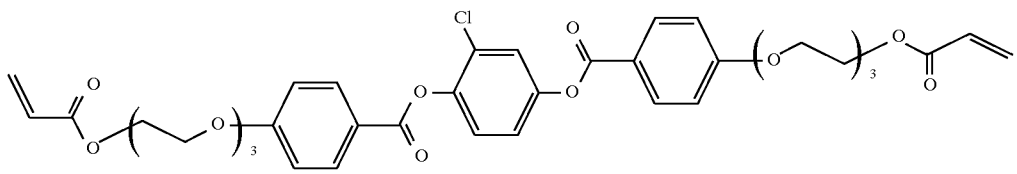

Phase behavior: S 45N 78 I

EXAMPLE 136

Mixture 37:
K1 as K1 of Example 135; concentration 23.75 mol %
K2 as K2 of Example 135; concentration 21.375 mol %
K3 as K3 of Example 135; concentration 2.375 mol %
K4 as K4 of Example 135; concentration 21.375 mol %
K5 as K5 of Example 135; concentration 19.2375 mol %
K6 as K6 of Example 135; concentration 2.1375 mol %
K7 as K7 of Example 135; concentration 2.375 mol %
K8 as K8 of Example 135; concentration 2.1375 mol %
K9 as K9 of Example 135; concentration 0.2375 mol %
K10 as K7 of Example 133; concentration 5 mol %
Phase behavior: S 43 Ch 70 I
Color: red

EXAMPLE 137

Mixture 38:
K1 as K1 of Example 135; concentration 23.25 mol %
K2 as K2 of Example 135; concentration 230.925 mol %
K3 as K3 of Example 135; concentration 2.325 mol %
K4 as K4 of Example 135; concentration 20.925 mol %
K5 as K5 of Example 135; concentration 18.8325 mol %
K6 as K6 of Example 135; concentration 2.0925 mol %
K7 as K7 of Example 135; concentration 2.325 mol %
K8 as K8 of Example 135; concentration 2.0925 mol %
K9 as K9 of Example 135; concentration 0.2325 mol %
K10 as K7 of Example 133; concentration 7 mol %
Phase behavior: S 41 Ch 70 I
Color: green

We claim:

1. A liquid-crystalline mixture comprising at least two different liquid-crystalline compounds of formula I:

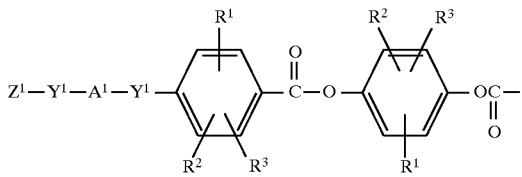

-continued

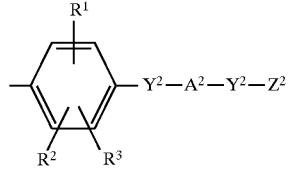

where
  $Z^1$ and $Z^2$, independently of one another, are polymerizable groups,
  $Y^1$ and $Y^2$, independently of one another, are each a direct bond, —O—, —COO—, —OCO—, or —S—,
  $A^1$ and $A^2$, independently of one another, are spacers, and
  $R^1$, $R^2$ and $R^3$, independently of one another are hydrogen, $C_1$- to $C_{20}$-alkyl, $C_1$- to $C_{20}$-alkoxy, $C_1$- to $C_{20}$-alkoxycarbonyl, $C_1$- to $C_{20}$-monoalkylaminocarbonyl, formyl, $C_1$- to $C_{20}$-alkylcarbonyl, fluorine, chlorine, bromine, cyano, $C_1$- to $C_{20}$-alkylcarbonyloxy, $C_1$- to $C_{20}$-alkylcarbonylamino, hydroxyl or nitro;
  wherein in at least one of said liquid crystalline compounds $A^1$ and $A^2$ are different from one another.

2. A liquid-crystalline mixture as claimed in claim 1, where $Z^1$ and/or $Z^2$ is a radical of the formula $CH_2=CH—$, $CH_2=CCl—$, $CH_2=C(CH_3)—$ or vinylphenyl.

3. A liquid-crystalline mixture as claimed in claim 1, where $Y^1$ and $Y^2$, independently of one another, are a direct bond, —O—, —COO— or —OCO—.

4. A liquid-crystalline mixture as claimed in claim 1, where $A^1$ and $A^2$, are $C_2$- to $C_{20}$-alkylene which may be interrupted by ether oxygen or ester groups, where the oxygen atoms or ester groups can replace third carbon atoms in the chain.

5. A liquid-crystalline mixture as claimed in claim 1, where $R^1$, $R^2$ and $R^3$, independently of one another, are hydrogen, $C_1$- to $C_{15}$-alkyl, $C_1$- to $C_{15}$-alkoxy, $C_1$- to $C_{15}$-alkoxycarbonyl, $C_1$- to $C_{15}$-monoalkylaminocarbonyl, formyl, $C_1$- to $C_{15}$-alkylcarbonyl, fluorine, chlorine, bromine, cyano, $C_1$- to $C_{15}$-alkylcarbonyloxy, $C_1$- to $C_{15}$-alkylcarbonylamino, hydroxyl or nitro.

6. A liquid-crystalline mixture as claimed in claim 5, where $R^1$, $R^2$ and $R^3$, independently of one another, are hydrogen, methyl, ethyl, $C_8$- to $C_{15}$-alkyl, methoxy, ethoxy, $C_8$- to $C_{15}$-alkoxy, methoxycarbonyl, ethoxycarbonyl, $C_8$- to $C_{15}$-alkoxycarbonyl, formyl, acetyl, $C_8$- to $C_{15}$-alkylcarbonyl, fluorine, chlorine, bromine, cyano, acetoxy, hydroxyl or nitro.

7. A liquid-crystalline mixture as claimed in claim 6, where $R^1$, $R^2$ and $R^3$, independently of one another, are hydrogen, methyl, ethyl, methoxy, ethoxy, methoxycarbonyl, formyl, acetyl, fluorine, chlorine, bromine, cyano, acetoxy, hydroxyl or nitro.

8. A liquid-crystalline mixture as claimed in claim 1, which comprises up to 50%, preferably from 1 to 30%, of polymerizable chiral compounds, which can be liquid-crystalline or non-liquid-crystalline.

9. A compound of the formula I as claimed in claim 1, where $R^1$ to $R^3$, $Z^1$, $Z^2$, $Y^1$, $Y^2$, $A^1$ and $A^2$ are as defined above, and —$A^1$—$Y^1$— and —$Y^2$—$A^2$— are not simultaneously identical —O—alkylene radicals.

10. A compound as claimed in claim 9, where $A^1$ and $A^2$ are different from one another.

11. A compound as claimed in claim 9, where $Z^1$ and $Z^2$ are different from one another.

12. A compound as claimed in claim 9, where radicals $Y^1$ and $Y^2$ are different from one another.

13. A compound of the formula in claim 1, where the moiety

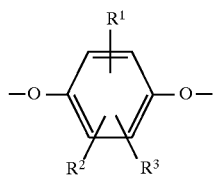

is

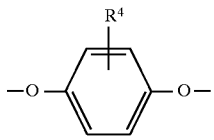

where $R^4$ is $C_2$- to $C_{15}$-alkyl, $C_2$- to $C_{15}$-alkoxy, $C_2$- to $C_{15}$-alkanoyl, $C_2$- to $C_{15}$-alkanoyloxy or $C_2$- to $C_{15}$-alkoxycarbonyl.

14. A compound as claimed in claim 13, where $R^4$ is $C_8$- to $C_{15}$-alkyl, $C_8$- to $C_{15}$-alkoxy, $C_8$- to $C_{15}$-alkanoyl, $C_8$- to $C_{15}$-alkanoyloxy or $C_8$- to $C_{15}$-alkoxycarbonyl.

15. A process of polymerizing a liquid crystalline mixture comprising:

providing a liquid crystalline mixture as claimed in claim 1, and;

free radical or ionic polymerizing the compounds of said mixture via said polymerizable groups.

16. The method of claim 15, wherein said mixture further comprises polymerizable chiral compounds.

* * * * *